US008993805B2

(12) United States Patent
Nishiyama et al.

(10) Patent No.: US 8,993,805 B2
(45) Date of Patent: Mar. 31, 2015

(54) BENZOFLUORENE COMPOUND AND USE THEREOF

(75) Inventors: Masakazu Nishiyama, Shunan (JP);
Naoki Matsumoto, Shunan (JP);
Takanori Miyazaki, Shunan (JP);
Takeshi Kanbara, Shunan (JP)

(73) Assignee: Tosoh Corporation, Shunan-shi (JP)

( * ) Notice: Subject to any disclaimer, the term of this patent is extended or adjusted under 35 U.S.C. 154(b) by 908 days.

(21) Appl. No.: 12/296,622

(22) PCT Filed: Apr. 12, 2007

(86) PCT No.: PCT/JP2007/058113
§ 371 (c)(1),
(2), (4) Date: Oct. 9, 2008

(87) PCT Pub. No.: WO2007/119800
PCT Pub. Date: Oct. 25, 2007

(65) Prior Publication Data
US 2009/0184312 A1 Jul. 23, 2009

(30) Foreign Application Priority Data

Apr. 13, 2006 (JP) ................................. 2006-110765
Jul. 24, 2006 (JP) ................................. 2006-201097

(51) Int. Cl.
*C07C 211/00* (2006.01)
*C07C 211/61* (2006.01)
*C09K 11/06* (2006.01)
*H01L 51/00* (2006.01)
*H05B 33/14* (2006.01)
*H01L 51/50* (2006.01)

(52) U.S. Cl.
CPC .............. *C07C 211/61* (2013.01); *C09K 11/06* (2013.01); *H01L 51/006* (2013.01); *H05B 33/14* (2013.01); *C07C 2103/40* (2013.01); *C07C 2103/94* (2013.01); *C07C 2103/97* (2013.01); *C09K 2211/1007* (2013.01); *C09K 2211/1011* (2013.01); *C09K 2211/1014* (2013.01); *H01L 51/0054* (2013.01); *H01L 51/5012* (2013.01); *H01L 51/5048* (2013.01); *H01L 51/5088* (2013.01)
USPC ....................................................... 564/305

(58) Field of Classification Search
None
See application file for complete search history.

(56) References Cited

U.S. PATENT DOCUMENTS

| 3,189,447 A | 6/1965 | Neugebauer et al. | |
| 3,257,203 A | 6/1966 | Sues et al. | |
| 5,147,880 A | 9/1992 | Jones | |
| 6,849,348 B2 * | 2/2005 | Zheng et al. | 428/690 |
| 2003/0143422 A1 | 7/2003 | Chen | |

| 2004/0131880 A1 | 7/2004 | Zheng et al. | |
| 2004/0131881 A1 | 7/2004 | Zheng et al. | |
| 2006/0152146 A1 | 7/2006 | Funahashi | |
| 2008/0160347 A1 * | 7/2008 | Wang et al. | 428/704 |

FOREIGN PATENT DOCUMENTS

| DE | 101 09 463 A1 | 10/2002 |
| EP | 0 832 881 A2 | 4/1998 |
| EP | 0 832 881 A3 | 4/1998 |
| EP | 1 724 294 A1 | 11/2006 |
| EP | 1 792 893 A1 | 6/2007 |
| JP | 51 93224 | 8/1976 |
| JP | 54 59143 | 5/1979 |
| JP | 55 108667 | 8/1980 |
| JP | 55 144250 | 11/1980 |
| JP | 56 119132 | 9/1981 |
| JP | 58 190953 | 11/1983 |
| JP | 59 195658 | 11/1984 |
| JP | 10 95972 | 4/1998 |
| JP | 10-161327 | 6/1998 |
| JP | 11 35532 | 2/1999 |
| JP | 2005 513713 | 5/2005 |
| WO | 2004/020387 A1 | 3/2004 |
| WO | 2004 061048 | 7/2004 |
| WO | 2005 056633 | 6/2005 |
| WO | 2006 025273 | 3/2006 |

OTHER PUBLICATIONS

Communication pursuant to Article 94(3)EPC issued Mar. 21, 2011, in European Patent Application No. 07 741 549.5-2103.
Bolton, Roger, "Substitution of 7H-Benzo [c] Fluorene", Journal of Chemical Research, Synopses , vol. 6, pp. 149-151 (1977).
O'Brien, D. F. et al., "Hole Transporting Materials With High Glass Transition Temperatures For Use In Organic Light-Emitting Devices", Advanced Materials, vol. 10, No. 14, pp. 1108-1112 (1998).
Shirota, Y. et al., "Starburst Molecules Based On π-Electron Systems As Materials For Organic Electroluminescent Devices", Journal of Luminescence, vol. 72-74, pp. 985-991 (1997).
Office Action issued Apr. 13, 2011, in Korean Patent Application No. 10-2008-7024196 (with English-language translation).
Office Action issued Jun. 15, 2011 in China Application No. 200780013331.7 (With English Translation).
Office Action issued on Aug. 19, 2011 in the corresponding Korean Patent Application No. 10-2011-7013541 (with English Translation).
Taiwanese Office Action issued on Apr. 22, 2011 in corresponding Taiwanese Application No. 096113001 (with an English Translation).
Office Action issued Oct. 19, 2011 in European Patent Application No. 07 741 549.5-2103.
Office Action issued Feb. 2, 2012 in Chinese Patent Application No. 200780013331.7 (with English translation).
Notice of Decision for Rejection issued Jan. 27, 2012 in Korean Patent Application No. 10-2008-7024196 (with English translation).
Notification of Reasons for Refusal issued Jul. 31, 2012 in Japanese Patent Application No. 2007-010813 (with English translation).
Notice of Decision for Rejection issued Mar. 20, 2012 in Korean Patent Application No. 10-2011-7013541 (with English translation).
Chinese Office Action issued May 3, 2012 in Patent Application No. 200780013331.7 with English Translation.
Japanese Office Action issued May 8, 2012 in Patent Application No. 2007-010813 with English Translation.
Communication of a notice of opposition issued Oct. 11, 2013, in Application No. / Patent No. 07741549.5-1454 / 2006278.
John F. Hartwig, "Transition Metal Catalyzed Synthesis of Arylamines and Aryl Ethers from Aryl Halides and Triflates : Scope and Mechanism", Angew. Chem. Int. Ed. 1998, 37, pp. 2046-2067.
Combined Chinese Office Action and Search Report issued Nov. 18, 2013 in Patent Application No. 201210113455.5 with English Translation and English Translation of Category of Cited Documents.

* cited by examiner

*Primary Examiner* — Clinton Brooks

(74) *Attorney, Agent, or Firm* — Oblon, McClelland, Maier & Neustadt, L.L.P.

(57) ABSTRACT

A novel material having high hole-transporting ability and a high glass transition temperature and having long-lasting durability is obtained.

A benzofluorene compound represented by formula (1) is used.

[Chem. 1]

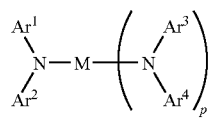

(1)

(In the formula, M is a substituted or unsubstituted aryl group having 6-40 carbon atoms or a substituted or unsubstituted heteroaryl group having 5-40 carbon atoms; $Ar^1$ to $Ar^4$ each independently is a substituted or unsubstituted aryl group having 6-40 carbon atoms or a substituted or unsubstituted heteroaryl group having 5-40 carbon atoms, provided that at least one of $Ar^1$ to $Ar^4$ is a substituent represented by any of the following formulae (2) to (5); and p is an integer of 0-2.)

[Chem. 2]

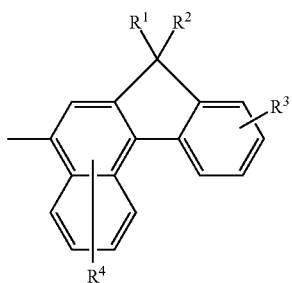

(2)

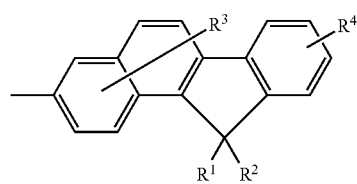

(3)

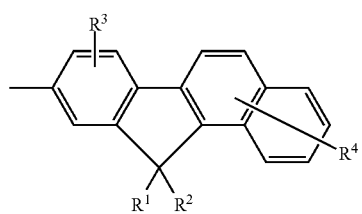

(4)

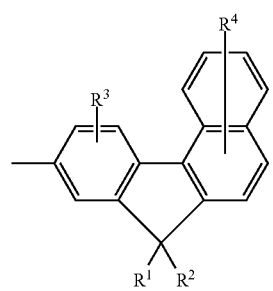

(5)

(In the formulae, $R^1$ to $R^4$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that $R^1$ and $R^2$ may be bonded to each other to form a ring.)

18 Claims, No Drawings

BENZOFLUORENE COMPOUND AND USE THEREOF

This application is a 371 of PCT/JP2007/058113, filed Apr. 12, 2007.

TECHNICAL FIELD

The present invention relates to a novel benzofluorene compound and a use thereof, in particular, an organic electroluminescent element. The benzofluorene compound is usable as a photosensitive material and an organic photoconductive material and, more specifically, can be used as a hole-transporting or hole-injecting material and a luminescent material in organic EL elements for use as flat light sources or displays or in electrophotographic photoreceptors, etc.

BACKGROUND ART

Organic photoconductive materials which have been developed as photosensitive materials or hole-transporting materials have many advantages including low cost, variety of processability, and non-polluting nature. Many compounds have been proposed. For example, materials such as oxadiazole derivatives (see, for example, patent document 1), oxazole derivatives (see, for example, patent document 2), hydrazone derivatives (see, for example, patent document 3), triarylpyrazoline derivatives (see, for example, patent documents 4 and 5), arylamine derivatives (see, for example, patent documents 6 and 7), and stilbene derivatives (see, for example, patent documents 8 and 9) have been disclosed.

Of these, starburst materials such as 4,4',4''-tris[N,N-(1-naphthyl)phenylamino]triphenylamine (1-TNATA) and 4,4',4''-tris[N,N-(m-tolyl)phenylamino]triphenylamine (MT-DATA) and biphenyl type arylamine derivatives such as 4,4'-bis[N-(1-naphthyl)-N-phenylamino]biphenyl (NPD) and 4,4'-bis[N-(m-tolyl)-N-phenylamino]biphenyl (TPD) are frequently used as hole-transporting or hole-injecting materials (see, for example, non-patent documents 1 and 2).

Furthermore, arylamine compounds employing a fluorene framework as a partial structure have also been proposed (see, for example, patent documents 10 and 11).

Moreover, an organic electroluminescent material having the same benzofluorene framework as in this patent has also been proposed (see, for example, patent document 12). However, this patent document includes no statement concerning a compound having an amino group directly bonded to the benzofluorenyl group. In addition, although patent document 12 includes a statement to the effect that a polymeric material having benzofluorenyl groups is especially useful as a luminescent material, there is no statement therein to the effect that the polymeric material is useful as a hole-transporting material and a hole-injecting material.

Patent Document 1: U.S. Pat. No. 3,189,447 (Claims)
Patent Document 2: U.S. Pat. No. 3,257,203 (Claims)
Patent Document 3: JP-A-54-59143 (Claims)
Patent Document 4: JP-A-51-93224 (Claims)
Patent Document 5: JP-A-55-108667 (Claims)
Patent Document 6: JP-A-55-144250 (Claims)
Patent Document 7: JP-A-56-119132 (Claims)
Patent Document 8: JP-A-58-190953 (Claims)
Patent Document 9: JP-A-59-195658 (Claims)
Patent Document 10: JP-A-11-35532 (Claims)
Patent Document 11: JP-A-10-95972 (Claims)
Patent Document 12: International Publication No. 2004/61048 Pamphlet (Claims)
Non-Patent Document 1: *Advanced Materials*, (Germany), 1998, Vol. 10, No. 14, pp. 1108-1112 (FIG. 1, Table 1)
Non-Patent Document 2: *Journal of Luminescence*, (Holland), 1997, 72-74, pp. 985-991 (FIG. 1)

DISCLOSURE OF THE INVENTION

Problems that the Invention is to Solve

However, those materials have drawbacks, for example, that they are poor in stability and durability, and are difficult to be considered as practically fully satisfactory materials. For example, NPD, which is a typical hole-transporting material and is presently superior in efficiency, etc., has a problem that it has a low glass transition temperature and this arouses troubles concerning element life. For example, the organic electroluminescent element abruptly ends its life. Furthermore, although investigations for the practical use of an organic electroluminescent element operated in the active-matrix mode are recently being made enthusiastically, a property required for this purpose is a lower operating voltage. With respect to this requirement, a fully satisfactory element has not been obtained with NPD. Consequently, there is a strong desire for a material which realizes a lower operating voltage and a longer life.

An object of the invention is to provide a novel material having a lower operating voltage and longer-lasting durability than conventional materials. More specifically, the object is to provide a novel benzofluorene compound suitable for use as a hole-injecting material, hole-transporting material, and luminescent material in organic EL elements, etc.

Means for Solving the Problems

The present inventors diligently made investigations. As a result, they have found that a benzofluorene compound represented by formula (1) is highly excellent in efficiency and durability. The invention has been thus completed. Namely, the invention relates to a benzofluorene compound represented by formula (1) and a use of the compound. Constitutions of the invention are described below.

1. A benzofluorene compound represented by formula (1):

[Chem. 1]

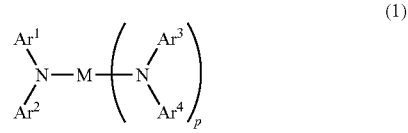

(1)

(wherein M is a substituted or unsubstituted aryl group having carbon atoms or a substituted or unsubstituted heteroaryl group having 5-40 carbon atoms; $Ar^1$ to $Ar^4$ each independently is a substituted or unsubstituted aryl group having 6-40 carbon atoms or a substituted or unsubstituted heteroaryl group having carbon atoms, provided that at least one of Ar¹ to Ar⁴ is a substituent represented by any of the following formulae (2) to (5); and p is an integer of 0-2)

[Chem. 2]

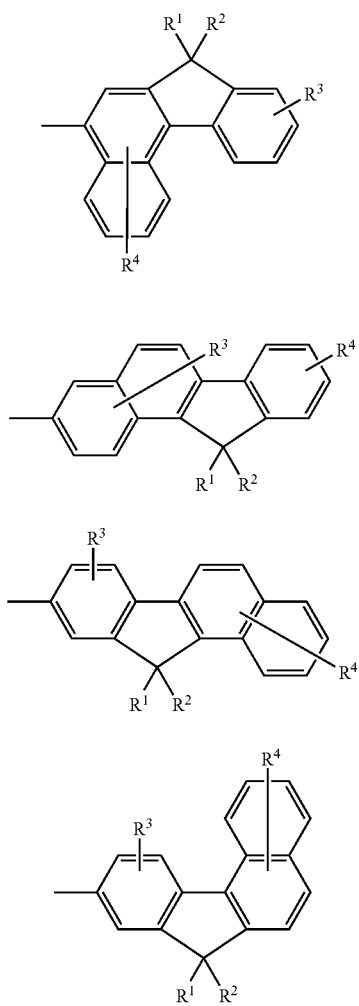

(wherein R¹ to R⁴ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that R¹ and R² may be bonded to each other to form a ring).

2. A benzo[c]fluorene compound represented by formula (1):

[Chem. 3]

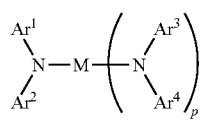

(1)

(wherein M is a substituted or unsubstituted aryl group having carbon atoms or a substituted or unsubstituted heteroaryl group having 5-40 carbon atoms; Ar¹ to Ar⁴ each independently is a substituted or unsubstituted aryl group having 6-40 carbon atoms or a substituted or unsubstituted heteroaryl group having carbon atoms, provided that at least one of Ar¹ to Ar⁴ is a substituent represented by the following formula (2); and p is an integer of 0-2)

[Chem. 4]

(2)

(wherein R¹ to R⁴ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that R¹ and R² may be bonded to each other to form a ring).

3. The benzo[c]fluorene compound represented by formula (1) as described under 2. above, wherein the formula (2) is the following formula (2'):

[Chem. 5]

(2')

(wherein R¹ to R⁴ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that R¹ and R² may be bonded to each other to form a ring).

4. The benzofluorene compound as described under 1. above, wherein M in formula (1) is one member selected from a mono-, di-, or trisubstituted benzene framework, biphenyl framework, fluorene framework, terphenyl framework, naphthalene framework, and spirofluorene framework.

5. A benzofluorene compound represented by the following formula (6), which is represented by formula (1) wherein p is 1 and M is a disubstituted biphenyl framework:

[Chem. 6]

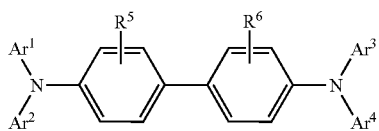
(6)

(wherein $R^5$ and $R^6$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms; and $Ar^1$ to $Ar^4$ are the same as defined in formula (1)).

6. A benzofluorene compound represented by any of formulae (7) to (10):

[Chem. 7]

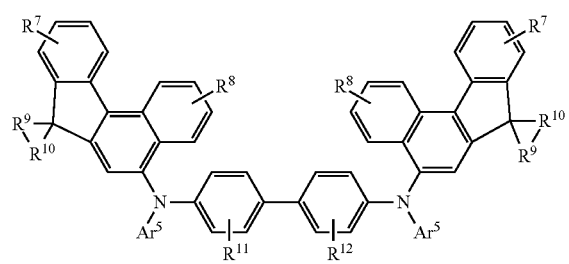
(7)

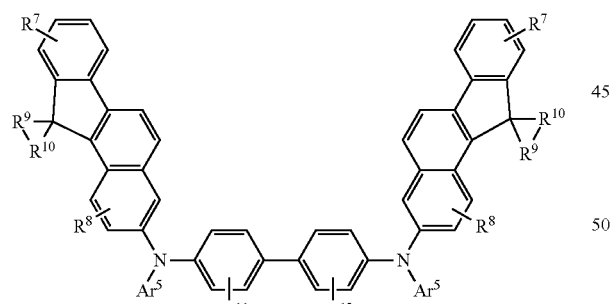
(8)

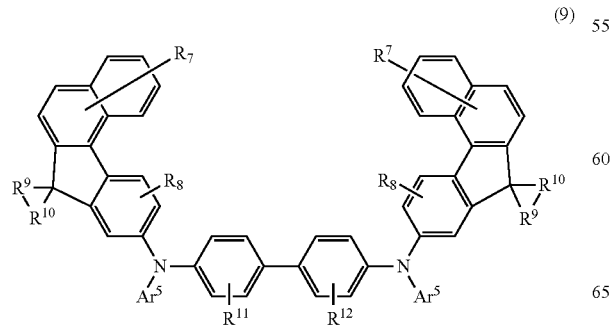
(9)

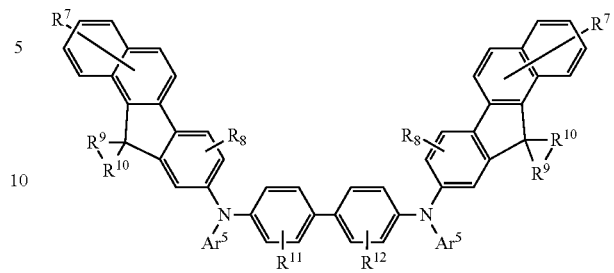
(10)

(wherein $R^7$, $R^8$, $R^{11}$, and $R^{12}$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms; $R^9$ and $R^{10}$ represent an alkylene group having 1-6 carbon atoms or an arylene group having 6-12 carbon atoms; and $Ar^5$ represents a substituted or unsubstituted aryl group having 6-40 carbon atoms or a substituted or unsubstituted heteroaryl group having 5-40 carbon atoms).

7. A halobenzofluorene compound represented by any of formulae (11) to (14):

[Chem. 8]

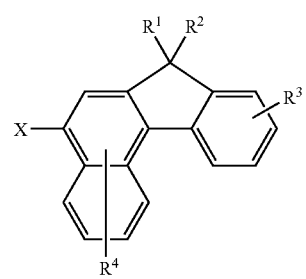
(11)

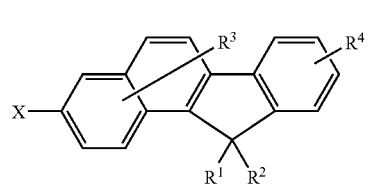
(12)

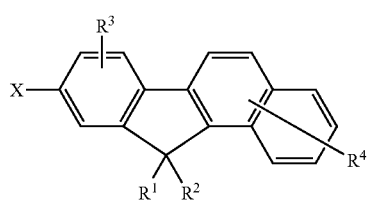
(13)

-continued (14)

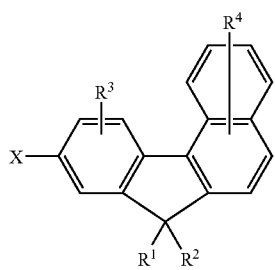

(wherein X represents an iodine, bromine, or chlorine atom; and R¹ to R⁴ each independently is a hydrogen atom, a halogen atom, a substituted or unsubstituted amino group, a linear, branched, or cyclic alkyl group, a linear, branched, or cyclic alkoxy group, a substituted or unsubstituted aryl group having carbon atoms, or a substituted or unsubstituted aryloxy group having 6-40 carbon atoms, provided that R¹ and R² may be bonded to each other to form a ring.)

8. An organic electroluminescent element characterized by employing the benzofluorene compound as described under 1. above or under 4, 5, or 6. above in any of a luminescent layer, a hole-transporting layer, and a hole-injecting layer.

Advantages of the Invention

The benzofluorene compound represented by formula (1) according to the invention has a lower operating voltage, higher power efficiency, and higher glass transition temperature than conventional materials. This compound can hence be expected to improve the life of elements or the like. Because of this, the compound can be used as, e.g., a hole-transporting material, hole-injecting material, or luminescent material in an organic EL element or an electrophotographic photoreceptor, etc.

BEST MODE FOR CARRYING OUT THE INVENTION

The invention will be explained below in detail.

In the benzofluorene compound represented by formula (1), M is a substituted or unsubstituted aryl group having carbon atoms or a substituted or unsubstituted heteroaryl group having 5-40 carbon atoms. Examples of the aryl group include mono-, di-, or trisubstituted benzene frameworks, biphenyl frameworks, terphenyl frameworks, naphthalene frameworks, fluorene frameworks, spirofluorene frameworks, and pyrene frameworks.

Examples of the heteroaryl group include mono-, di-, or trisubstituted carbazole frameworks, oxazole frameworks, oxadiazole frameworks, and thiazole frameworks. M may have one or more substituents selected, for example, from alkyl groups such as methyl group, ethyl group, and propyl group, halogen atoms such as fluorine atom, chlorine atom, iodine atom, and bromine atom, alkoxy groups such as methoxy group and ethoxy group, aryl groups such as phenyl group, naphthyl group, and biphenyl group, and heteroaryl groups such as pyridyl group, thienyl group, and carbazoyl group.

In particular, the benzofluorene compound preferably is one represented by formula (4) in which M is a disubstituted benzene framework, biphenyl framework, fluorene framework, terphenyl framework, naphthalene framework, or spirofluorene framework, because this compound is high in hole mobility, which is a factor necessary for realizing a voltage reduction.

In formula (1), Ar¹ to Ar⁴ each independently is a substituted or unsubstituted aryl group having 6-40 carbon atoms or a substituted or unsubstituted heteroaryl group having carbon atoms, provided that at least one of Ar¹ to Ar⁴ is a substituent represented by any of the following formulae (2) to (5).

[Chem. 9]

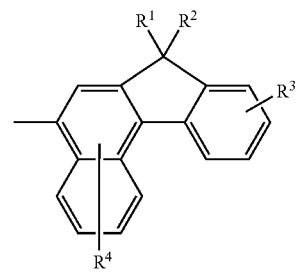

(2)

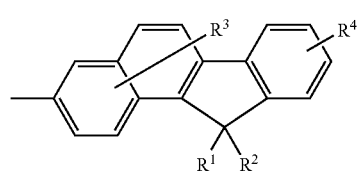

(3)

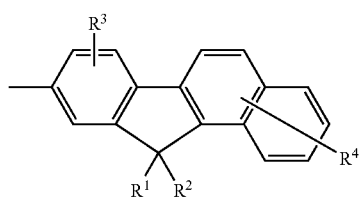

(4)

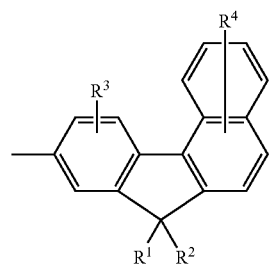

(5)

(In the formulae, R¹ to R⁴ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that R¹ and R² may be bonded to each other to form a ring.)

Examples of the substituted or unsubstituted aryl groups having 6-40 carbon atoms represented by Ar¹ to Ar⁴ include phenyl group, 1-naphthyl group, 2-naphthyl group, 2-anthryl group, 9-anthryl group, 2-fluorenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-isopropylphenyl group, 2-isopropylphenyl group, 4-n-butylphenyl group, 4-isobutylphenyl group, 4-sec-butylphenyl group, 2-sec-butylphenyl group, 4-tert-butylphenyl group, 3-tert-butylphenyl group, 2-tertbutylphenyl group, 4-n-pentylphenyl group, 4-isopentylphenyl group, 2-neopentylphenyl group, 4-tert-pentylphenyl group, 4-n-hexylphenyl group, 4-(2'-ethylbutyl)phenyl group, 4-n-heptylphenyl group, 4-n-octylphenyl group, 4-(2'-ethylhexyl)phenyl group, 4-tert-octylphenyl group, 4-n-decylphenyl group, 4-n-dodecylphenyl group, 4-n-tetradecylphenyl group, 4-cyclopentylphenyl group, 4-cyclohexylphenyl group, 4-(4'-methylcyclohexyl)phenyl group, 4-(4'-tert-butylcyclohexyl)phenyl group, 3-cyclohexylphenyl group, 2-cyclohexylphenyl group, 4-ethyl-1-naphthyl group, 6-n-butyl-2-naphthyl group, 2,4-dimethylphenyl group, 2,5-dimethylphenyl group, 3,4-dimethylphenyl group, 3,5-dimethylphenyl group, 2,6-dimethylphenyl group, 2,4-diethylphenyl group, 2,3,5-trimethylphenyl group, 2,3,6-trimethylphenyl group, 3,4,5-trimethylphenyl group, 2,6-diethylphenyl group, 2,5-diisopropylphenyl group, 2,6-diisobutylphenyl group, 2,4-di-tert-butylphenyl group, 2,5-di-tert-butylphenyl group, 4,6-di-tert-butyl-2-methylphenyl group, 5-tert-butyl-2-methylphenyl group, 4-tert-butyl-2,6-dimethylphenyl group, 9-methyl-2-fluorenyl group, 9-ethyl-2-fluorenyl group, 9-n-hexyl-2-fluorenyl group, 9,9-dimethyl-2-fluorenyl group, 9,9-diethyl-2-fluorenyl group, 9,9-di-n-propyl-2-fluorenyl group, 4-methoxyphenyl group, 3-methoxyphenyl group, 2-methoxyphenyl group, 4-ethoxyphenyl group, 3-ethoxyphenyl group, 2-ethoxyphenyl group, 4-n-propoxyphenyl group, 3-n-propoxyphenyl group, 4-isopropoxyphenyl group, 2-isopropoxyphenyl group, 4-n-butoxyphenyl group, 4-isobutoxyphenyl group, 2-sec-butoxyphenyl group, 4-n-pentyloxyphenyl group, 4-isopentyloxyphenyl group, 2-isopentyloxyphenyl group, 4-neopentyloxyphenyl group, 2-neopentyloxyphenyl group, 4-n-hexyloxyphenyl group, 2-(2'-ethylbutyl)oxyphenyl group, 4-n-octyloxyphenyl group, 4-n-decyloxyphenyl group, 4-n-dodecyloxyphenyl group, 4-n-tetradecyloxyphenyl group, 4-cyclohexyloxyphenyl group, 2-cyclohexyloxyphenyl group, 2-methoxy-1-naphthyl group, 4-methoxy-1-naphthyl group, 4-n-butoxy-1-naphthyl group, 5-ethoxy-1-naphthyl group, 6-methoxy-2-naphthyl group, 6-ethoxy-2-naphthyl group, 6-n-butoxy-2-naphthyl group, 6-n-hexyloxy-2-naphthyl group, 7-mehoxy-2-naphthyl group, 7-n-butoxy-2-naphthyl group, 2-methyl-4-methoxyphenyl group, 2-methyl-5-methoxyphenyl group, 3-methyl-4-methoxyphenyl group, 3-methyl-5-methoxyphenyl group, 3-ethyl-5-methoxyphenyl group, 2-methoxy-4-methylphenyl group, 3-methoxy-4-methylphenyl group, 2,4-dimethoxyphenyl group, 2,5-dimethoxyphenyl group, 2,6-dimethoxyphenyl group, 3,4-dimethoxyphenyl group, 3,5-dimethoxyphenyl group, 3,5-diethoxyphenyl group, 3,5-di-n-butoxyphenyl group, 2-methoxy-4-ethoxyphenyl group, 2-methoxy-6-ethoxyphenyl group, 3,4,5-trimethoxyphenyl group, 4-phenylphenyl group, 3-phenylphenyl group, 2-phenylphenyl group, 4-(4'-methylphenyl)phenyl group, 4-(3'-methylphenyl)phenyl group, 4-(4'-methoxyphenyl)phenyl group, 4-(4'-n-butoxyphenyl)phenyl group, 2-(2'-methoxyphenyl)phenyl group, 4-(4'-chlorophenyl)phenyl group, 3-methyl-4-phenylphenyl group, 3-methoxy-4-phenylphenyl group, 9-phenyl-2-fluorenyl group, 4-fluorophenyl group, 3-fluorophenyl group, 2-fluorophenyl group, 4-chlorophenyl group, 3-chlorophenyl group, 2-chlorophenyl group, 4-bromophenyl group, 2-bromophenyl group, 4-chloro-1-naphthyl group, 4-chloro-2-naphthyl group, 6-bromo-2-naphthyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3-dichlorophenyl group, 2,4-dichlorophenyl group, 2,5-dichlorophenyl group, 3,4-dichlorophenyl group, 3,5-dichlorophenyl group, 2,5-dibromophenyl group, 2,4,6-trichlorophenyl group, 2,4-dichloro-1-naphthyl group, 1,6-dichloro-2-naphthyl group, 2-fluoro-4-methylphenyl group, 2-fluoro-5-methylphenyl group, 3-fluoro-2-methylphenyl group, 3-fluoro-4-methylphenyl group, 2-methyl-4-fluorophenyl group, 2-methyl-5-fluorophenyl group, 3-methyl-4-fluorophenyl group, 2-chloro-4-methylphenyl group, 2-chloro-5-methylphenyl group, 2-chloro-6-methylphenyl group, 2-methyl-3-chlorophenyl group, 2-methyl-4-chlorophenyl group, 3-chloro-4-methylphenyl group, 3-methyl-4-chlorophenyl group, 2-chloro-4,6-dimethylphenyl group, 2-methoxy-4-fluorophenyl group, 2-fluoro-4-methoxyphenyl group, 2-fluoro-4-ethoxyphenyl group, 2-fluoro-6-methoxyphenyl group, 3-fluoro-4-ethoxyphenyl group, 3-chloro-4-methoxyphenyl group, 2-methoxy-5-chlorophenyl group, 3-methoxy-6-chlorophenyl group, and 5-chloro-2,4-dimethoxyphenyl group. However, the aryl groups should not be construed as being limited to those examples.

The substituted or unsubstituted heteroaryl groups having 5-40 carbon atoms represented by $Ar^1$ to $Ar^4$ each may be an aromatic group containing at least one heteroatom selected from oxygen, nitrogen, and sulfur atoms. Examples thereof include heterocyclic groups such as 4-quinolyl group, 4-pyridyl group, 3-pyridyl group, 2-pyridyl group, 3-furyl group, 2-furyl group, 3-thienyl group, 2-thienyl group, 2-oxazolyl group, 2-thiazolyl group, 2-benzoxazolyl group, 2-benzthiazolyl group, and 2-benzimidazolyl group. However, the heteroaryl groups should not be construed as being limited to those examples.

In formulae (2) to (5), $R^1$ to $R^4$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that $R^1$ and $R^2$ may be bonded to each other to form a ring.

Examples of the linear, branched, or cyclic alkyl groups represented by $R^1$ to $R^4$ include linear, branched, or cyclic alkyl groups having 1-18 carbon atoms. Specific examples thereof include methyl group, ethyl group, propyl group, isopropyl group, butyl group, sec-butyl group, tert-butyl group, pentyl group, hexyl group, heptyl group, octyl group, stearyl group, trichloromethyl group, trifluoromethyl group, cyclopropyl group, cyclohexyl group, 1,3-cyclohexadienyl group, and 2-cyclopenten-1-yl group.

Examples of the linear, branched, or cyclic alkoxy groups represented by $R^1$ to $R^4$ include linear, branched, or cyclic alkoxy groups having 1-18 carbon atoms. Specific examples thereof include methoxy group, ethoxy group, propoxy group, isopropoxy group, n-butoxy group, sec-butoxy group, tert-butoxy group, pentyloxy group, hexyloxy group, stearyloxy group, and trifluoromethoxy group.

Examples of the substituted or unsubstituted aryl groups having 6-40 carbon atoms represented by $R^1$ to $R^4$ include phenyl group, 4-methylphenyl group, 3-methylphenyl group, 2-methylphenyl group, 4-ethylphenyl group, 3-ethylphenyl group, 2-ethylphenyl group, 4-n-propylphenyl group, 4-n-butylphenyl group, 4-isobutylphenyl group, 4-tert-butylphenyl group, 4-cyclopentylphenyl group, 4-cyclohexylphenyl group, 2,4-dimethylphenyl group, 3,5-dimethylphenyl group, 3,4-dimethylphenyl group, 4-(1-naphthyl)phenyl group, 4-(9-anthryl)phenyl group, 4-(10-phenyl-9-anthryl)phenyl group, 4-biphenyl group, 1-naphthyl group, 2-naphthyl group, 9-phenanthryl group, 9-anthryl group, 10-phenyl-9-anthryl group, 10-biphenyl-9-anthryl group, 9,9-dimethylfluoren-2-yl group, and 7-phenyl-9,9- dimethylfluoren-2-yl group. Examples thereof further include the substituents enumerated above as examples of $Ar^1$ to $Ar^4$.

Examples of the substituted or unsubstituted aryloxy groups having 6-40 carbon atoms represented by $R^1$ to $R^4$ include phenoxy group, p-tert-butylphenoxy group, 3-fluorophenoxy group, and 4-fluorophenoxy group.

Examples of the halogen atoms represented by $R^1$ to $R^4$ include fluorine, chlorine, bromine, and iodine atoms.

Examples of the substituted or unsubstituted amino groups represented by $R^1$ to $R^4$ include monosubstituted amino groups such as methylamino group, ethylamino group, phenylamino group, m-tolylamino group, p-tolylamino group, 1-naphthylamino group, 2-naphthylamino group, and 4-biphenylamino group, dimethylamino group, diethylamino group, dipropylamino group, dibutylamino group, diphenylamino group, di(m-tolyl)amino group, di(p-tolyl)amino group, N-(m-tolyl)phenylamino group, N-(p-tolyl)phenylamino group, N-(1-naphthyl)phenylamino group, N-(2-naphthyl)phenylamino group, N-(4-biphenyl)phenylamino group, di(4-biphenyl)amino group, di(2-naphthyl)amino group, bis(acetoxymethyl)amino group, bis(acetoxyethyl)amino group, bis(acetoxypropyl)amino group, bis(acetoxybutyl)amino group, and dibenzylamino group. However, the amino groups should not be construed as being limited to those substituents.

Preferred examples of the invention are benzofluorene compounds represented by formula (1) in which p is 1 and M is a disubstituted biphenyl framework or terphenyl framework. More preferred examples are benzofluorene compounds in which M is a disubstituted biphenyl framework, i.e., ones represented by formula (6).

Even more preferred examples are benzofluorene compounds represented by formula (6) in which either of $Ar^1$ and $Ar^2$ and either of $Ar^3$ and $Ar^4$ are groups each represented by any of formulae (2) to (5). Especially preferred are benzofluorene compounds represented by formula (6) which satisfies $Ar^1=Ar^3$ and $Ar^2=Ar^4$ and in which either of $Ar^1$ and $Ar^2$ is any of formulae (2) to (5).

In formulae (2) to (5), $R^1$ and $R^2$ may be bonded to each other to form a ring. Examples of such compound include a benzofluorene compound represented by any of the following formulae (7) to (10). This compound is especially preferred from the standpoints of element efficiency and durability.

Benzofluorene compounds having as a partial structure a substituent represented by formula (2), among the substituents represented by formulae (2) to (5), are preferred because they can be easily synthesized. Especially preferred of these are benzofluorene compounds having a substituent represented by the following formula (2') as a partial structure.

[Chem. 10]

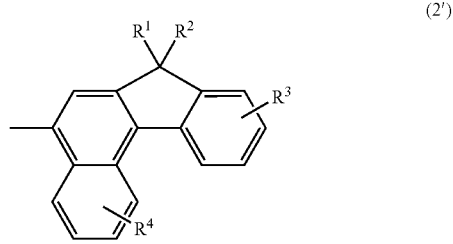

(2')

(In the formula, $R^1$ to $R^4$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms, provided that $R^1$ and $R^2$ may be bonded to each other to form a ring.)

[Chem. 11]

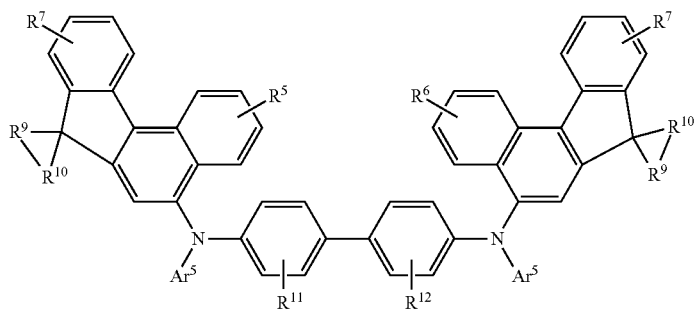

(7)

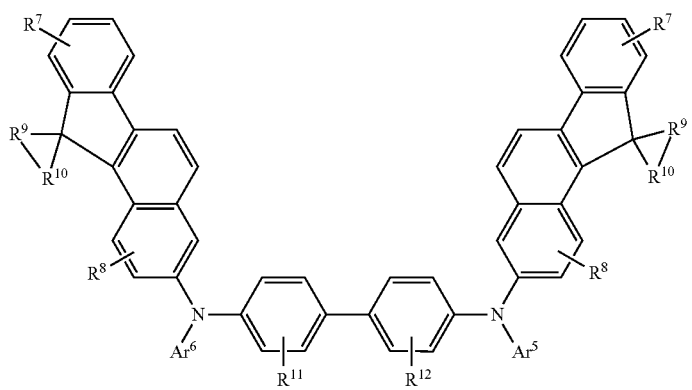

(8)

(9)

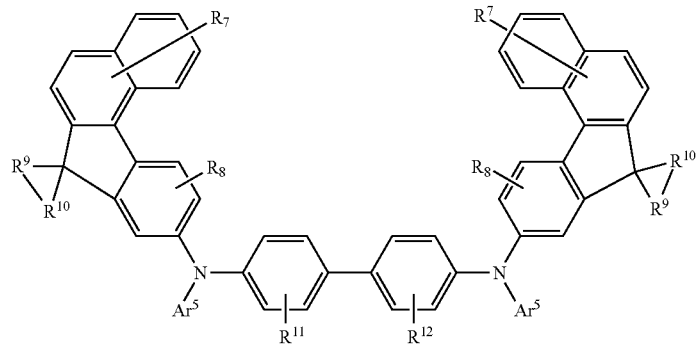

(10)

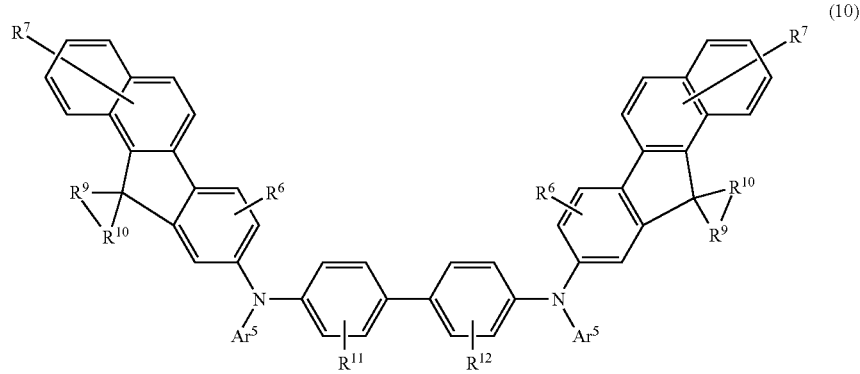

(In the formulae, $R^7$, $R^8$, $R^{11}$, and $R^{12}$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms; $R^9$ and $R^{10}$ represent an alkylene group having 1-6 carbon atoms or an arylene group having 6-12 carbon atoms; and $Ar^5$ represents a substituted or unsubstituted aryl group having 6-40 carbon atoms or a substituted or unsubstituted heteroaryl group having 5-40 carbon atoms.)

In the benzofluorene compounds represented by formulae (7) to (10), examples of $R^7$, $R^8$, $R^{11}$, and $R^{12}$ include the same substituents as $R^3$ to $R^6$ represented by formulae (2) to (6). Examples of $R^9$ and $R^{10}$ include alkylene groups such as methylene group, ethylene group, trimethylene group, and tetraethylene group and arylene groups such as phenylene group and naphthylene group. Examples of the substituted or unsubstituted aryl group having 6-40 carbon atoms or the substituted or unsubstituted heteroaryl group having 5-40 carbon atoms each represented by $Ar^5$ include the same substituents as M represented by formula (1).

Preferred compounds are shown below as examples. However, the compound of the invention should not be construed as being limited to the following compounds.

[Chem. 12]

(A1)

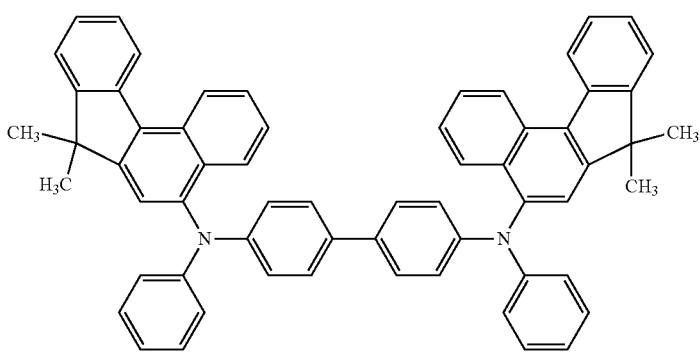

-continued
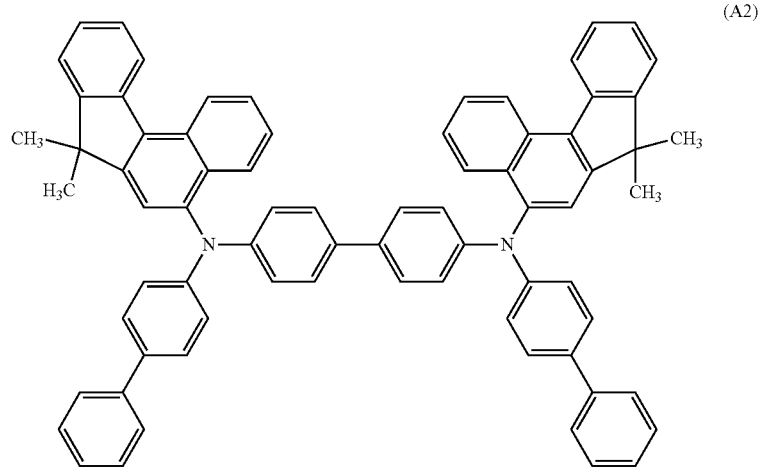
(A2)
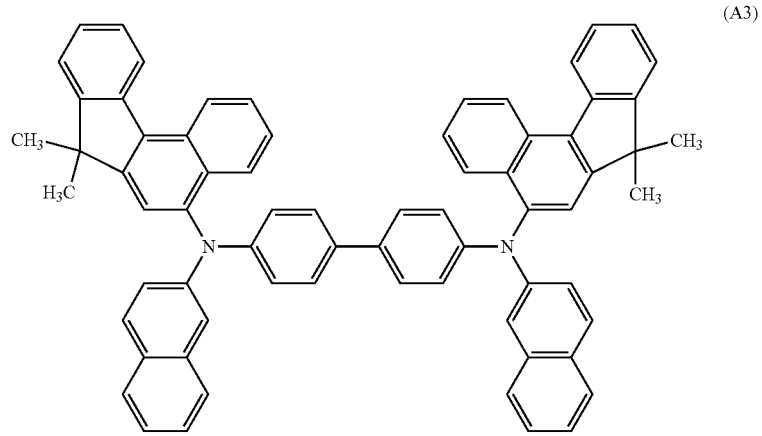
(A3)
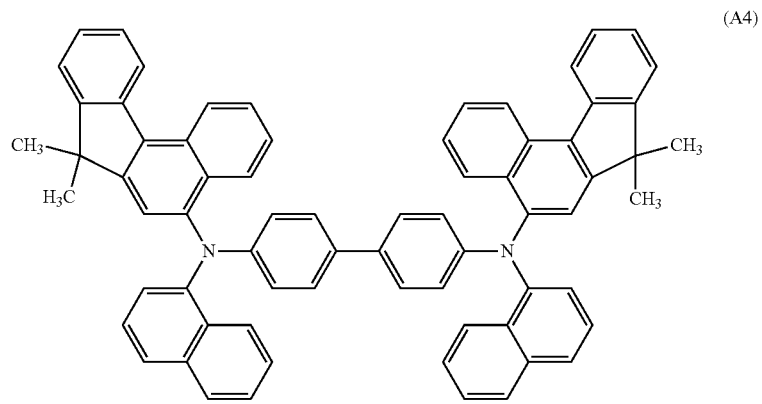
(A4)
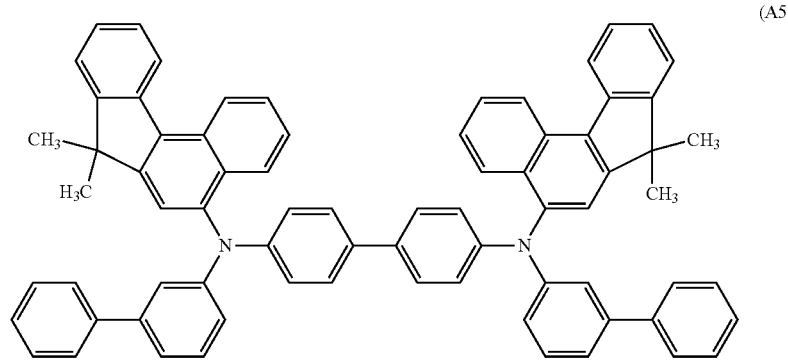
(A5)

-continued
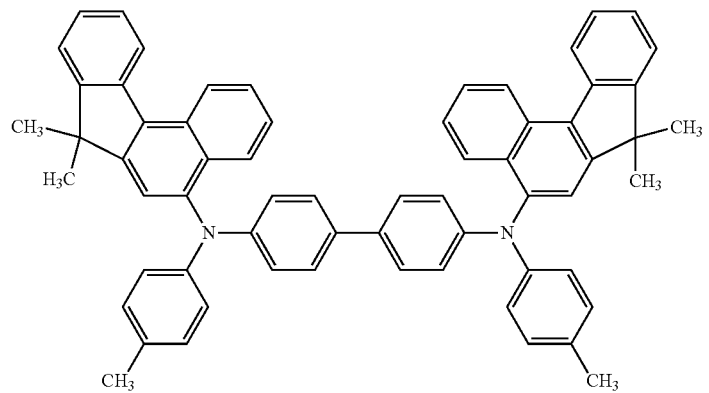
(A6)
[Chem. 13]
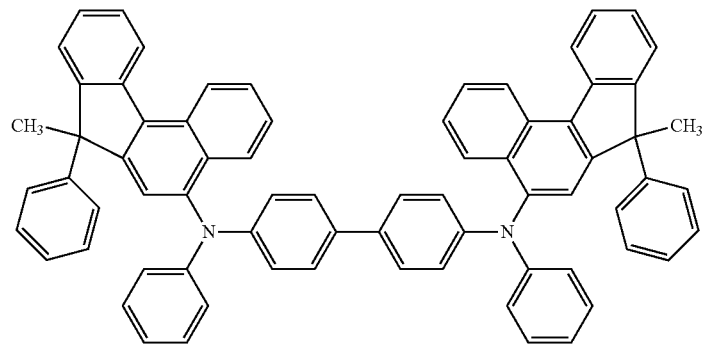
(B1)
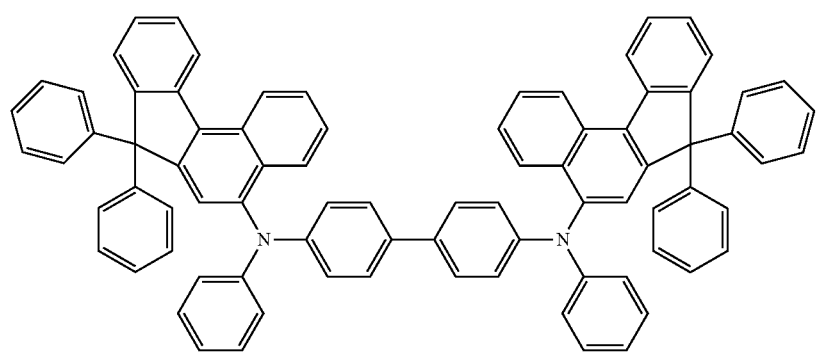
(B2)
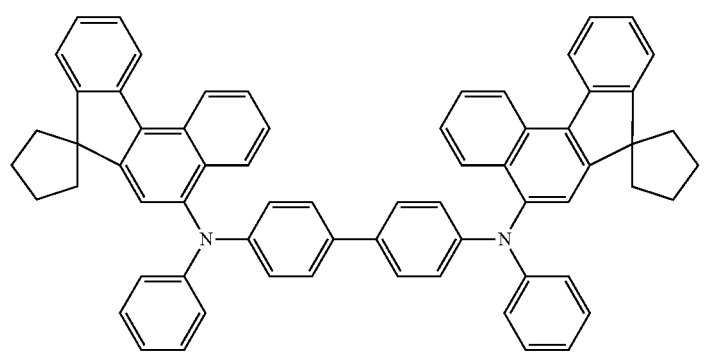
(B3)

-continued
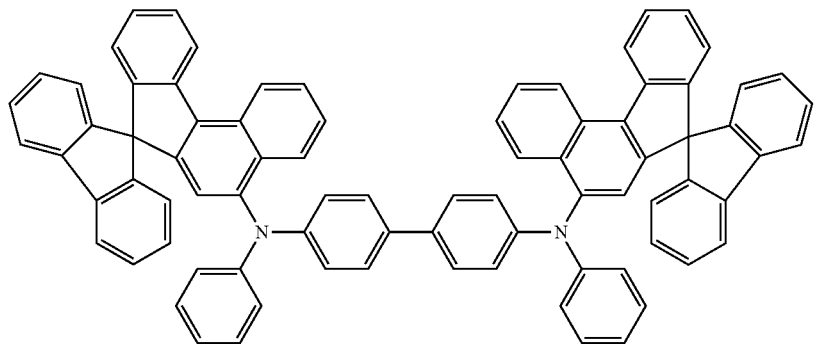
(B4)
[Chem. 14]
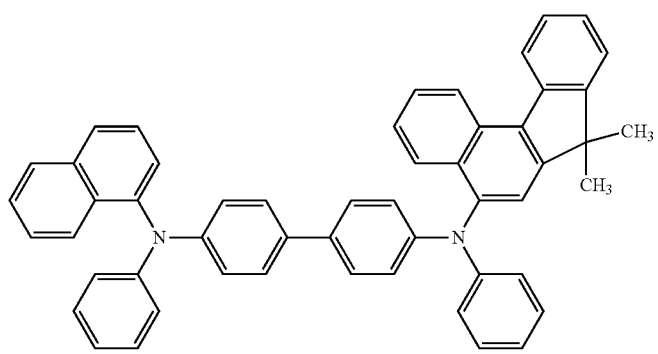
(C1)
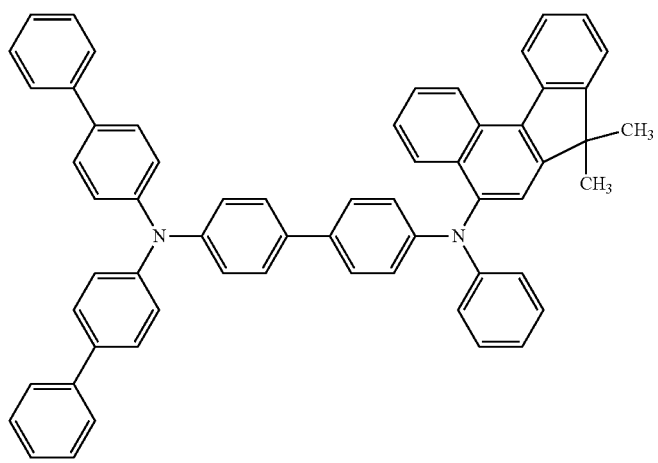
(C2)
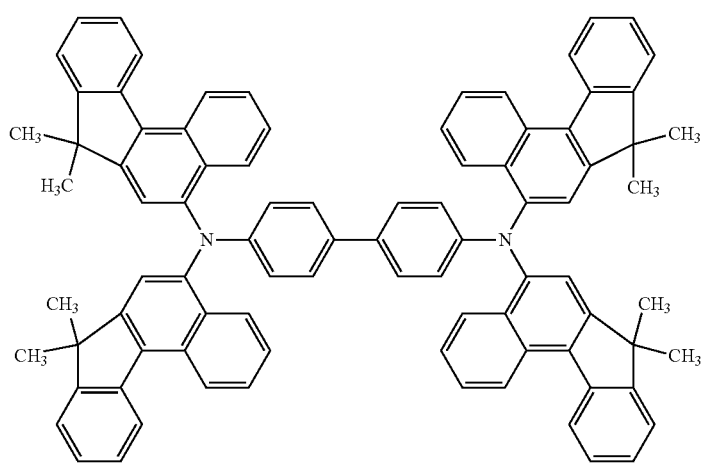
(C3)

(C4)
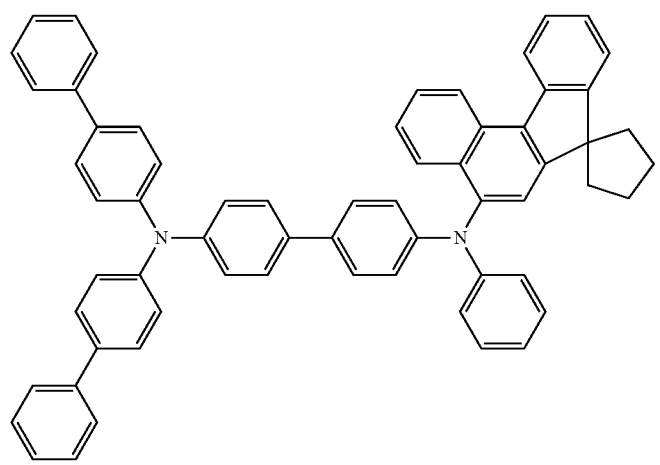
[Chem. 15]
(D1)
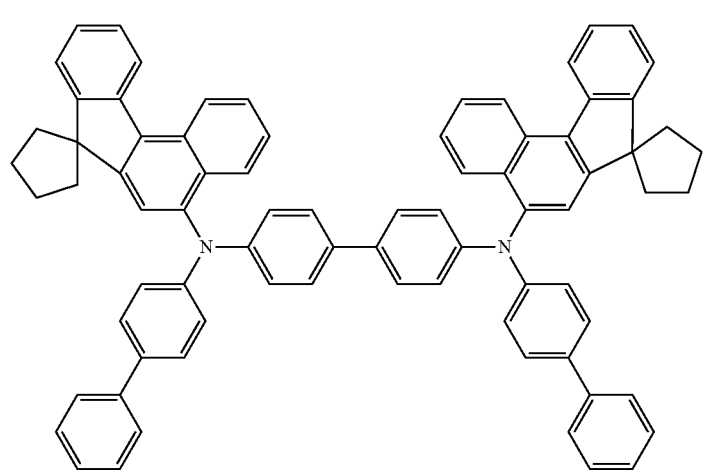
(D2)
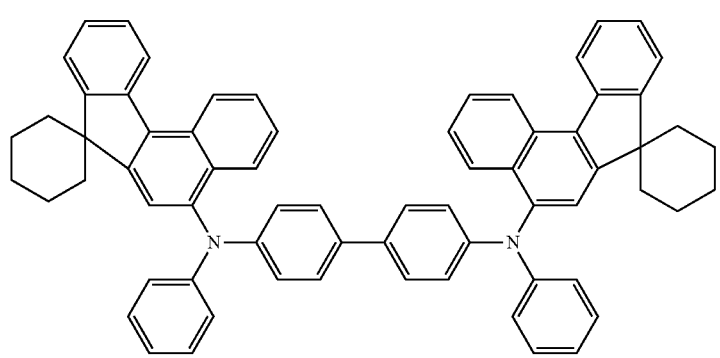

(D3)
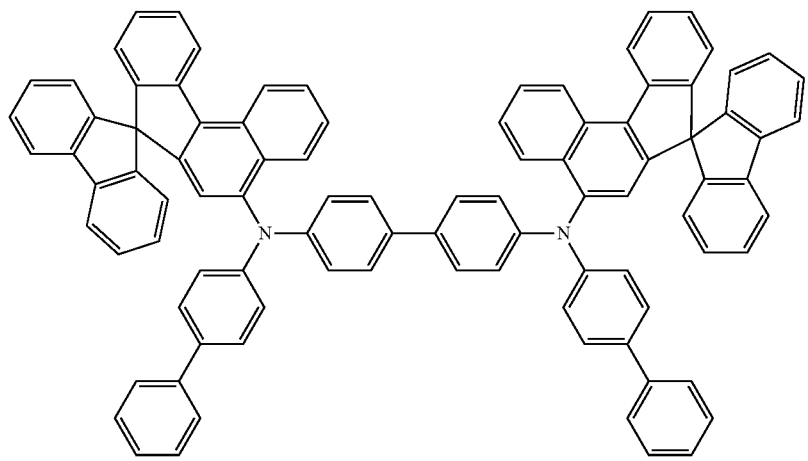
(D4)
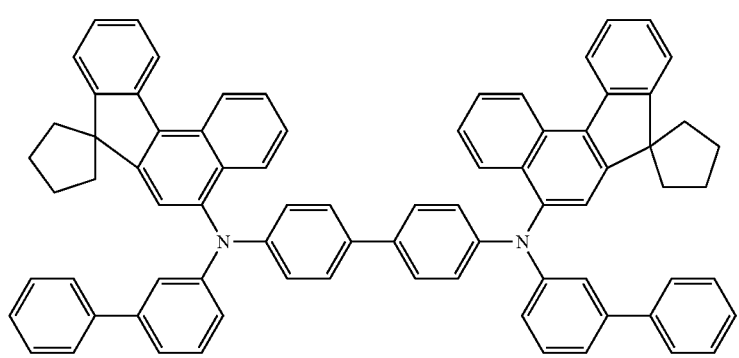
[Chem. 16]
(E1)
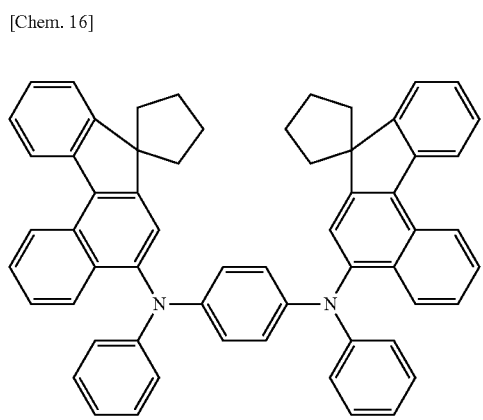
(E2)
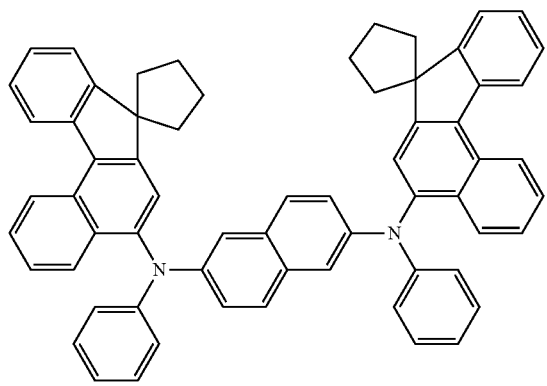

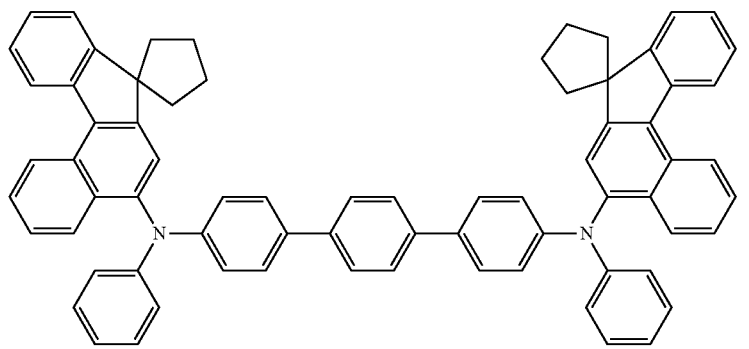
(E3)
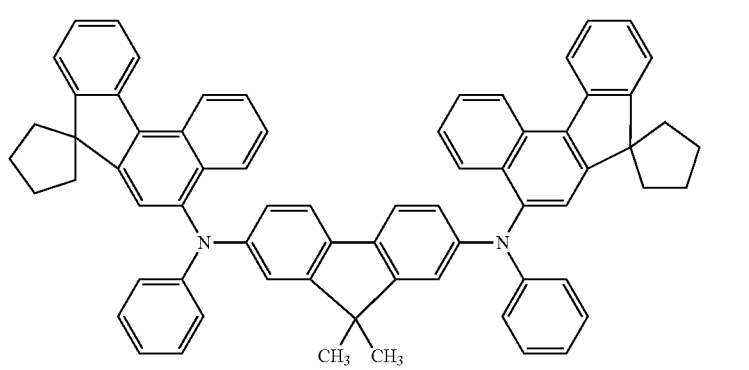
(E4)
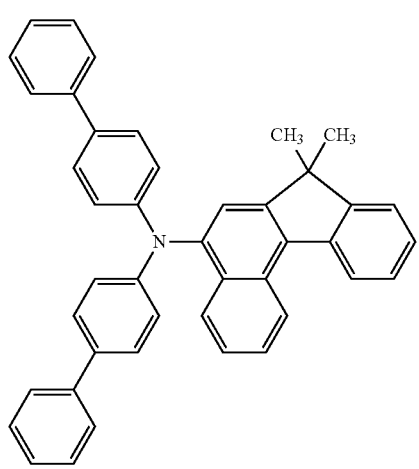
(E5)
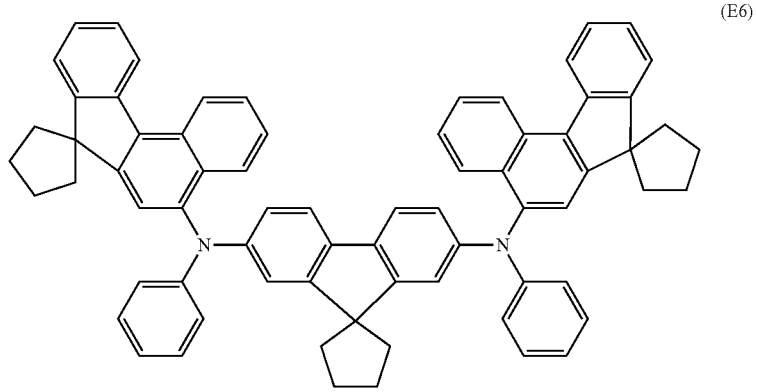
(E6)

(E7)
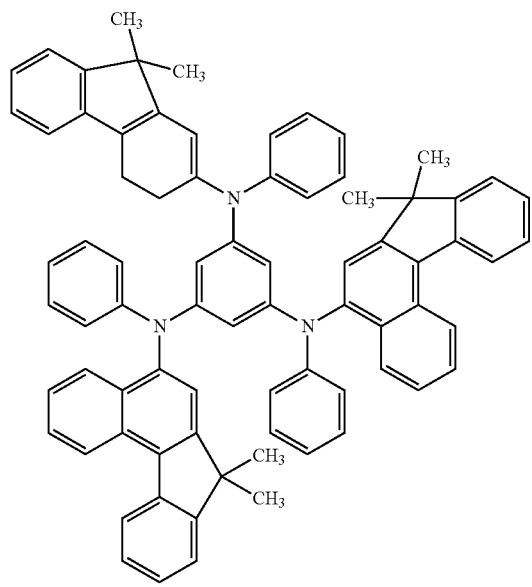
[Chem. 17]
(F1)
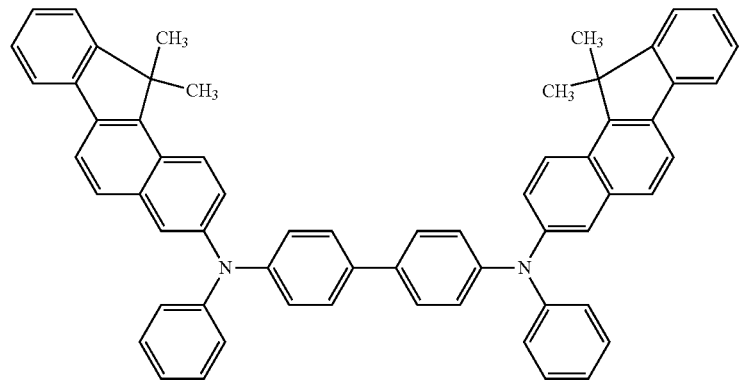
(F2)
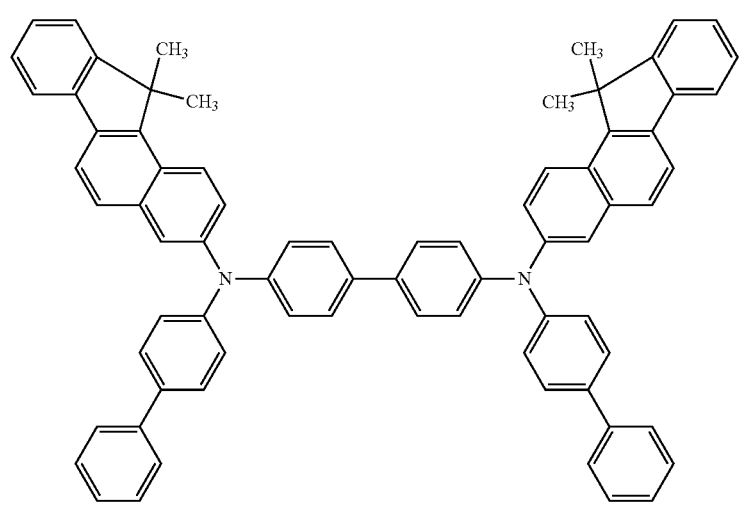

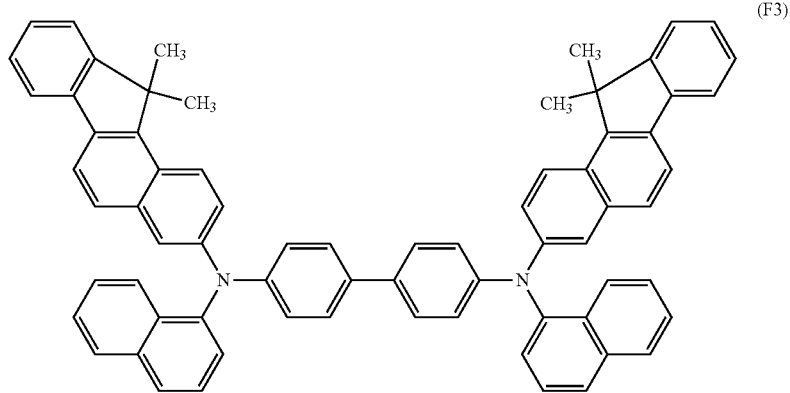
(F3)
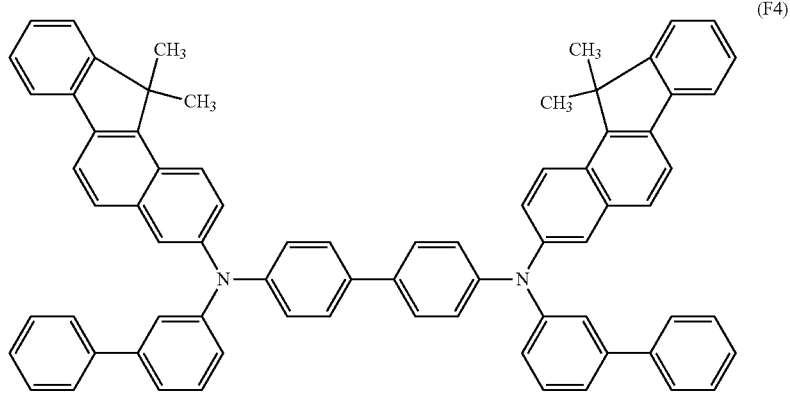
(F4)
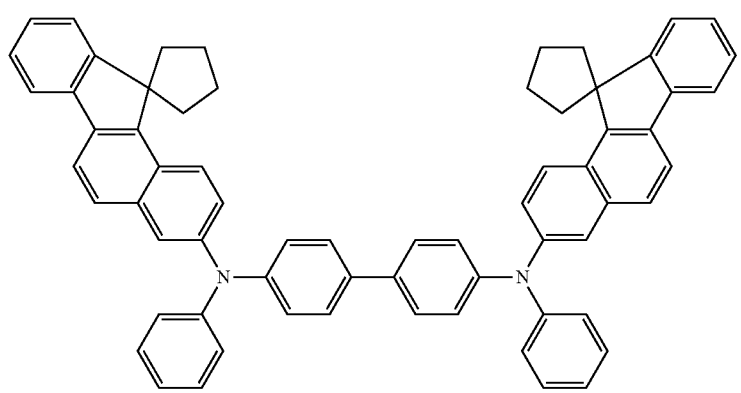
(F5)
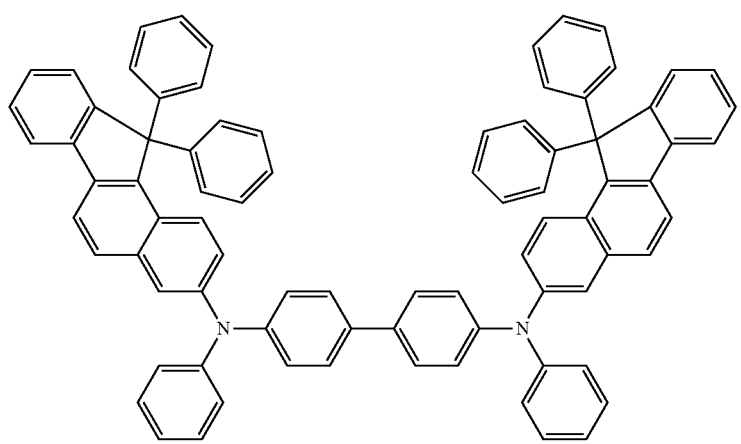
(F6)

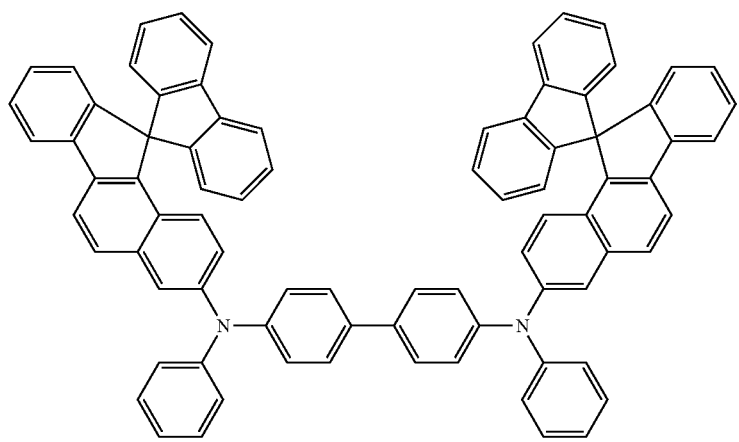
(F7)
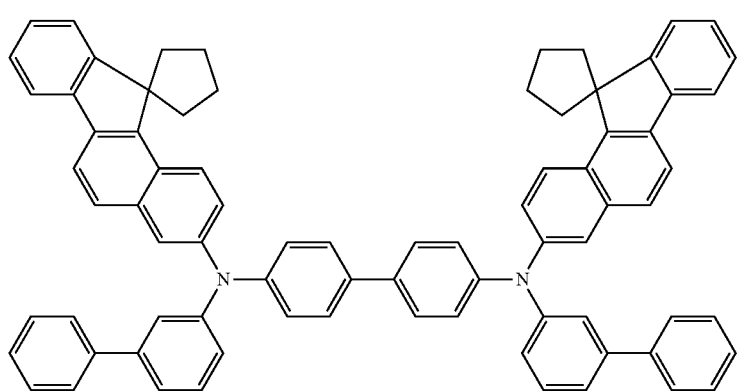
(F8)
[Chem. 18]
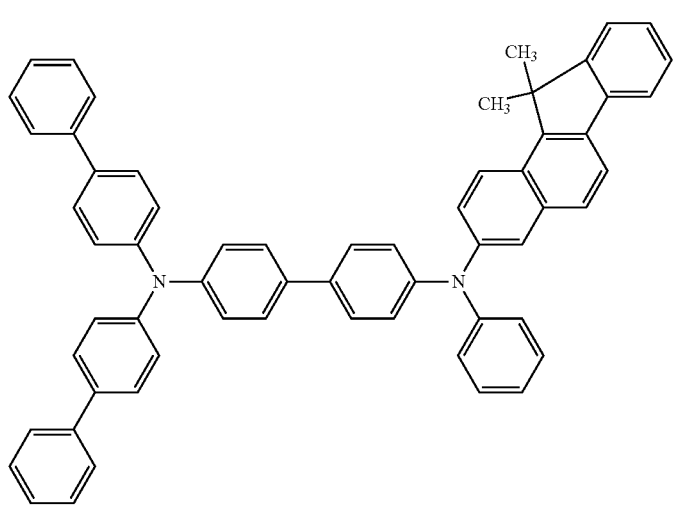
(G1)

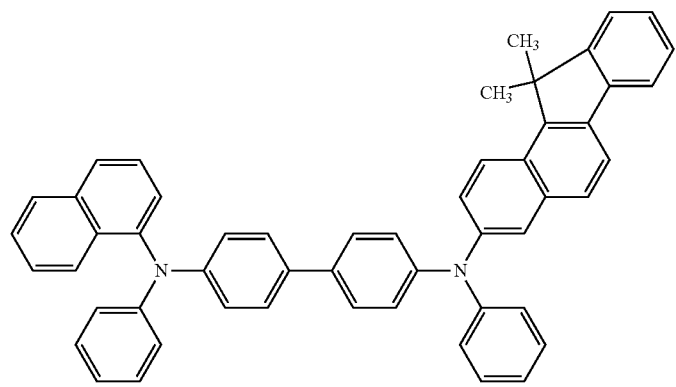
(G2)
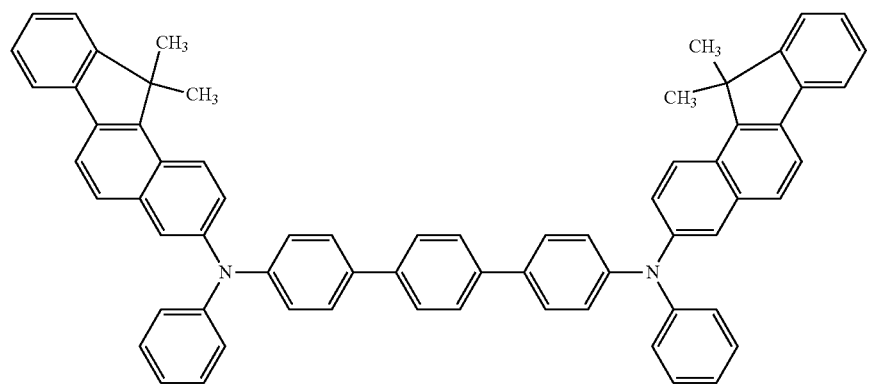
(G3)
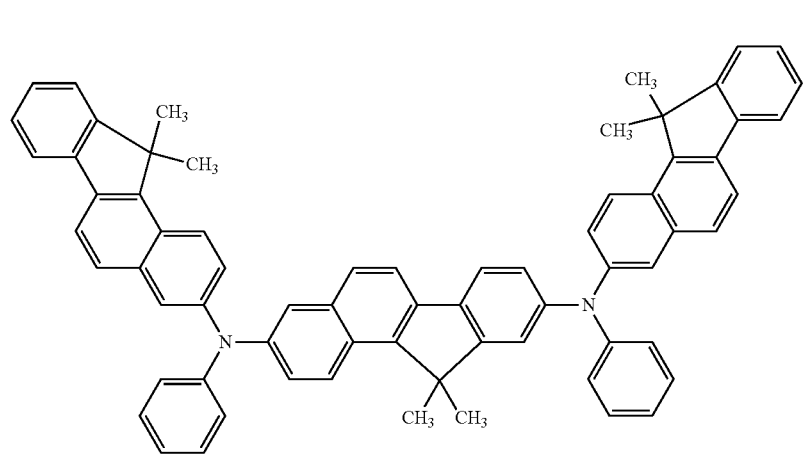
(G4)

(G5)
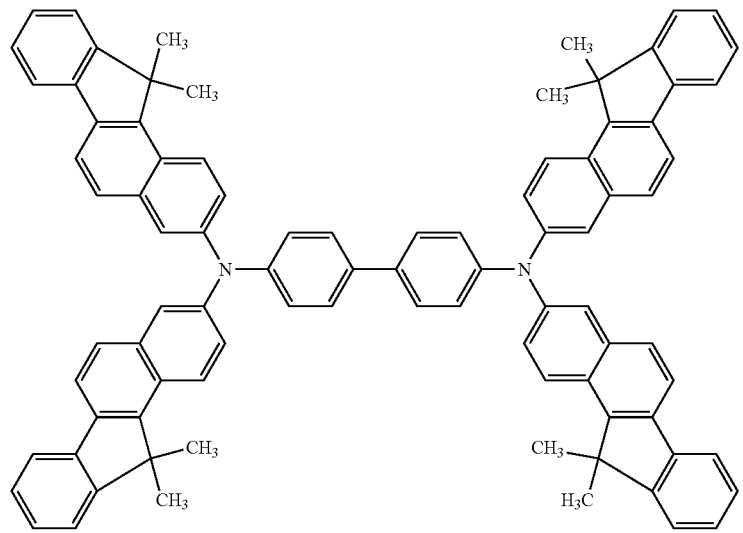
(G6)
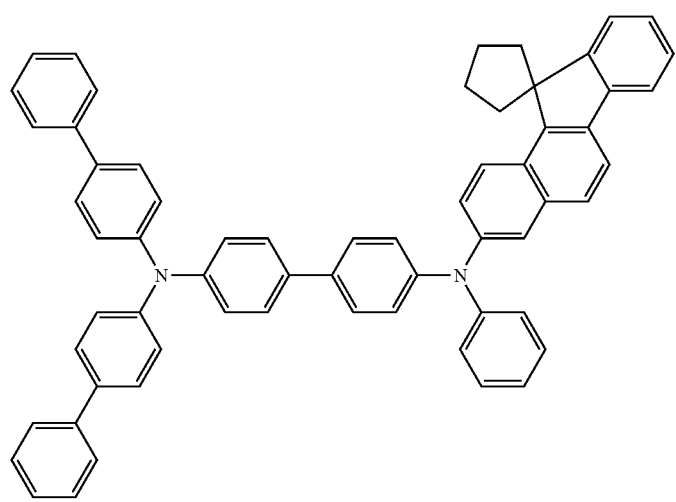
(G7)
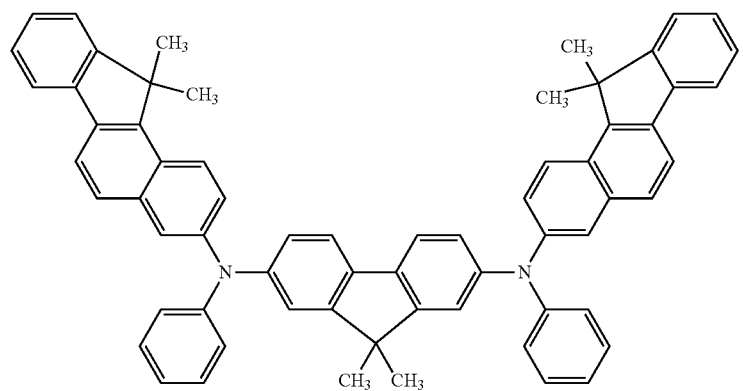

(G8)
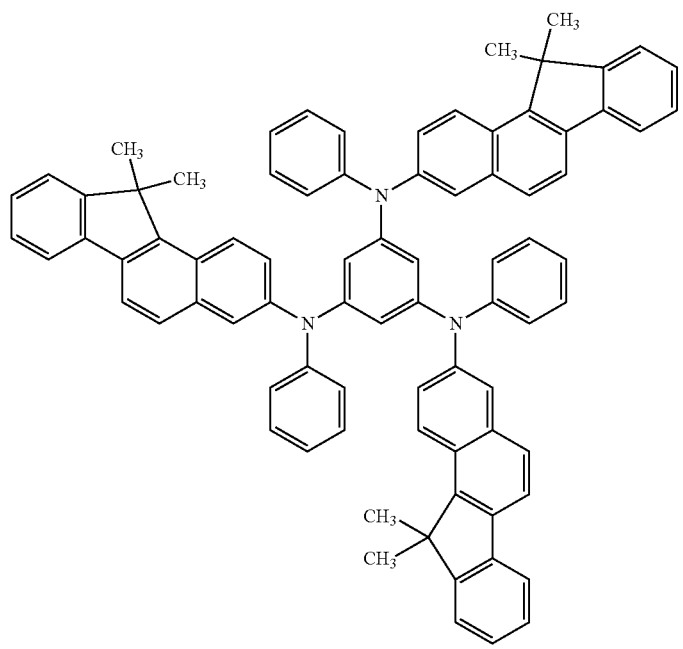
[Chem. 19]
(H1)
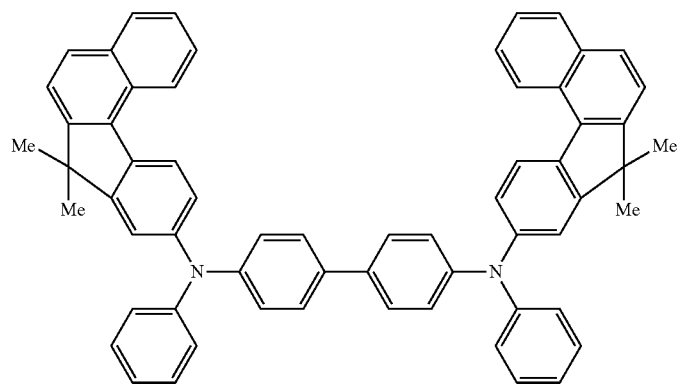
(H2)
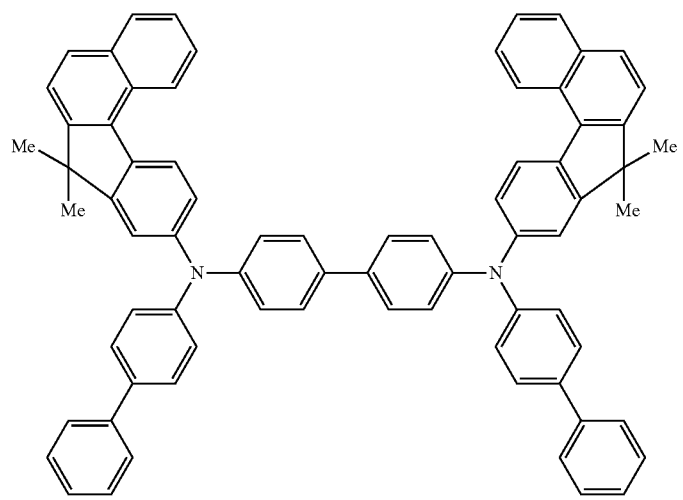

(H3)
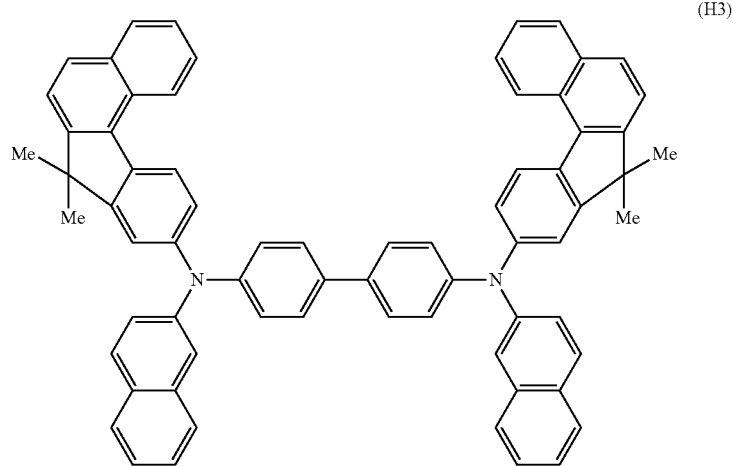
(H4)
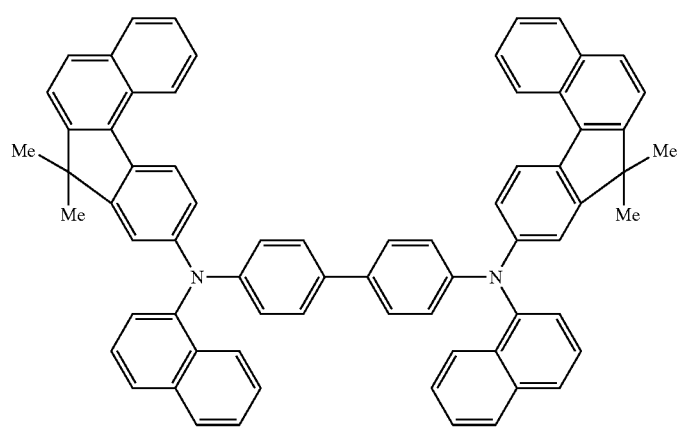
(H5)
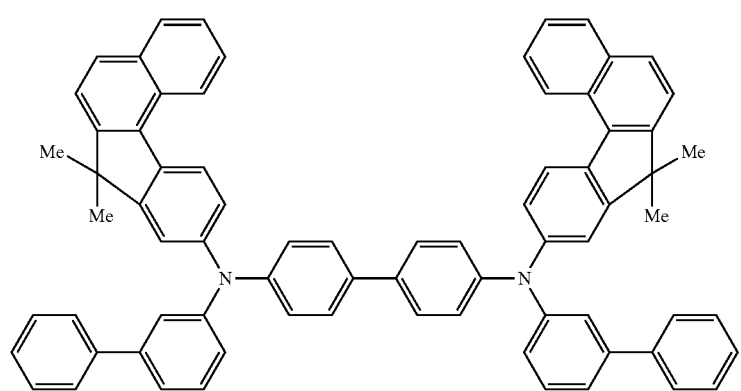

-continued
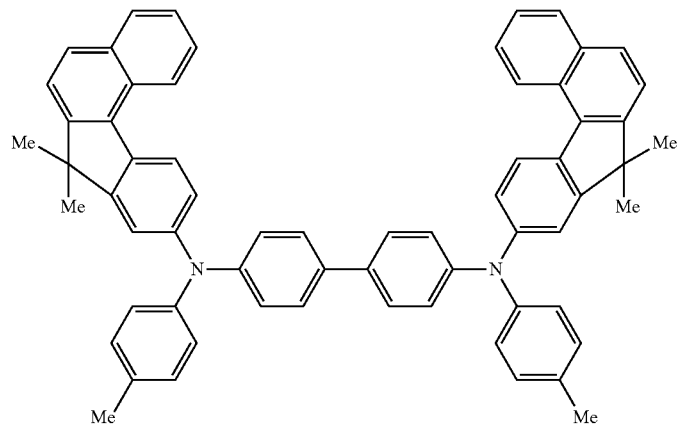
(H6)
[Chem. 20]
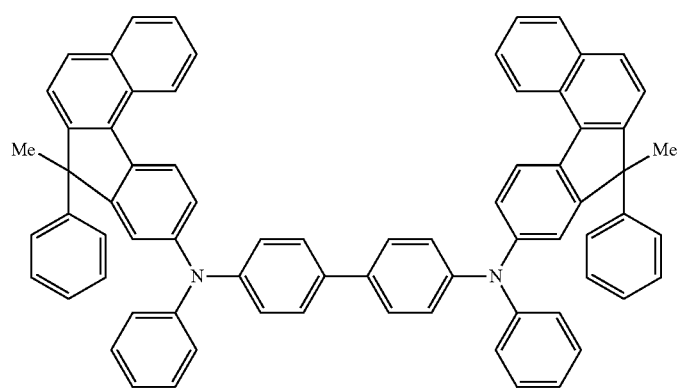
(I1)
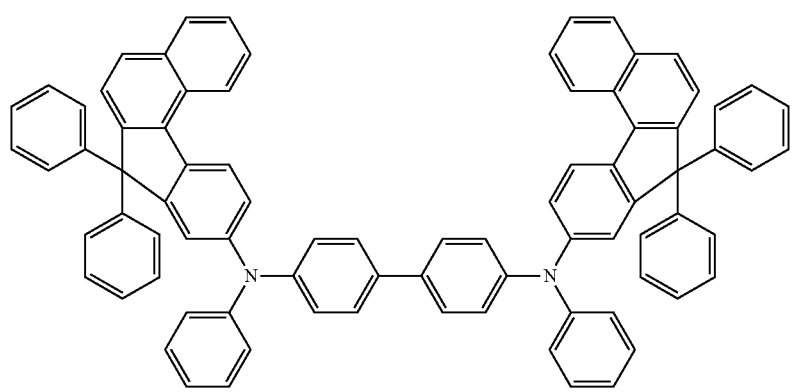
(I2)
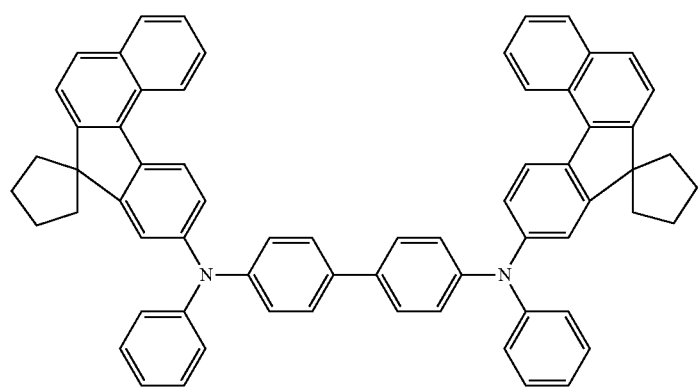
(I3)

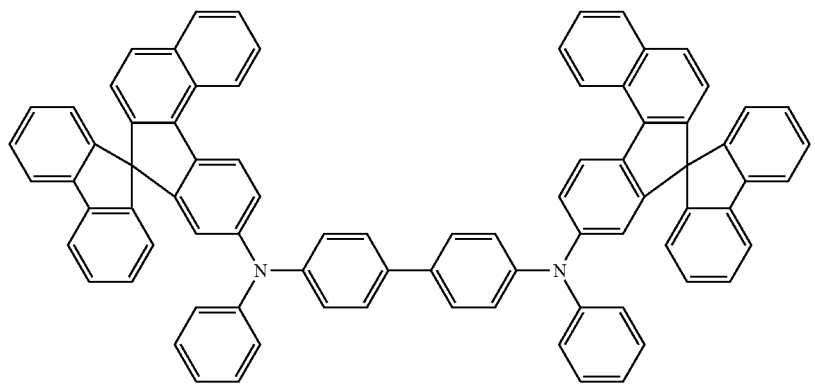
(I4)
[Chem. 21]
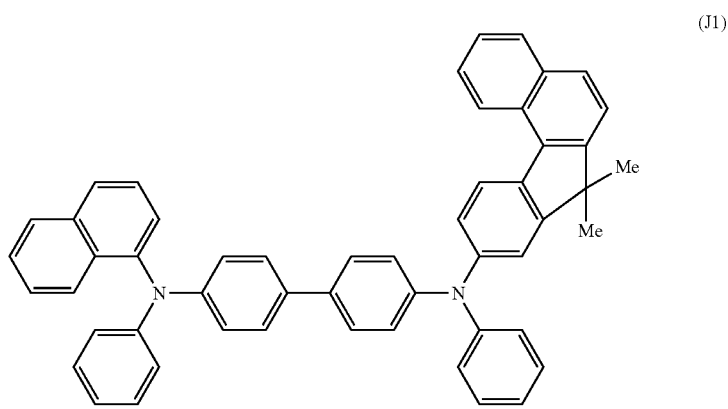
(J1)
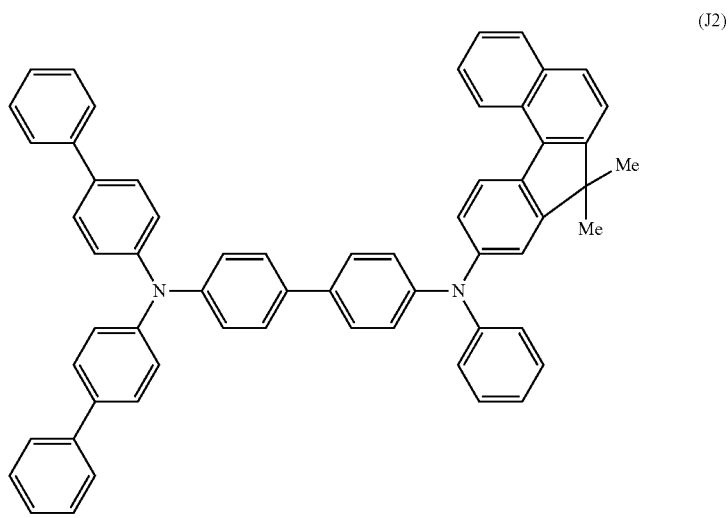
(J2)

-continued
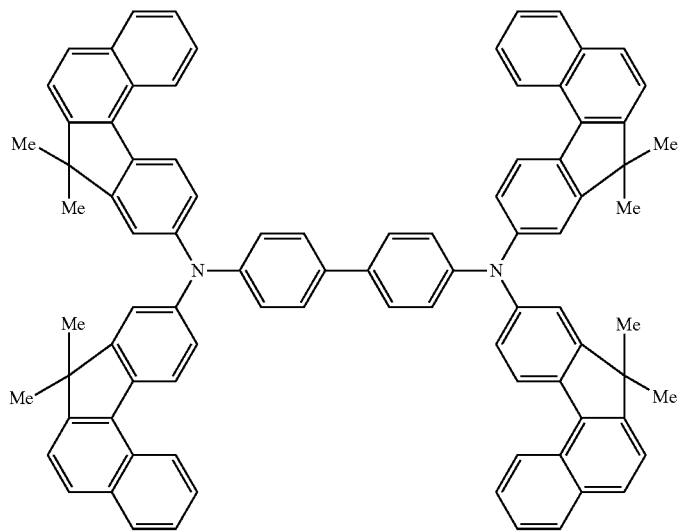
(J3)
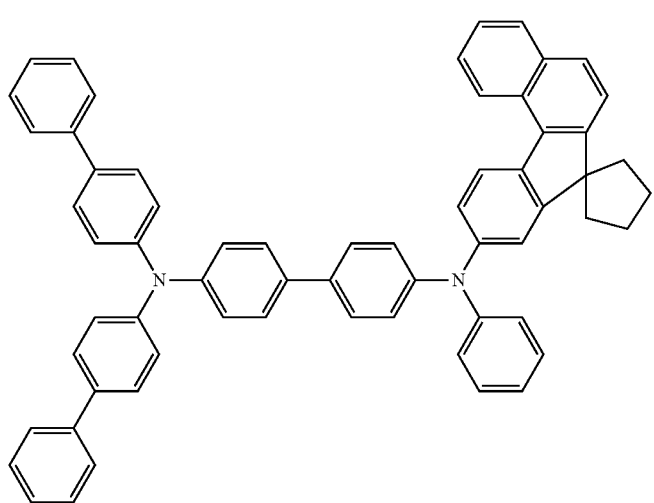
(J4)
[Chem. 22]
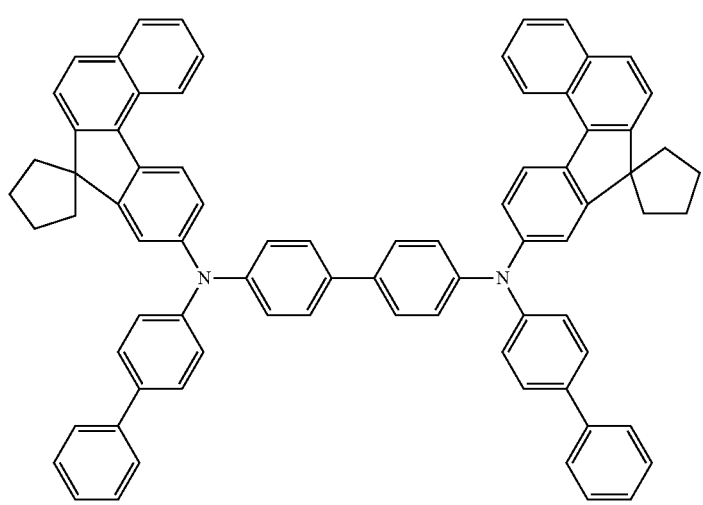
(K1)

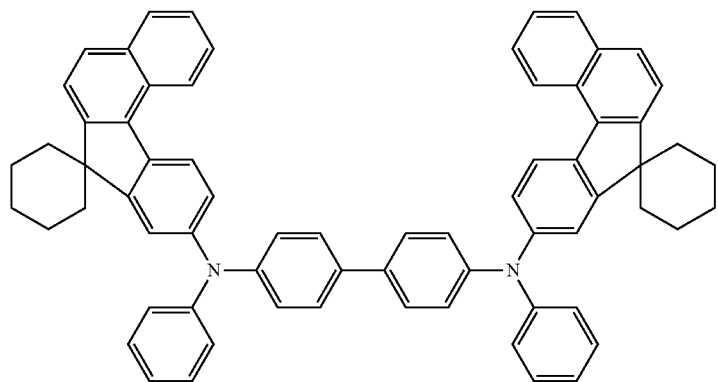
(K2)
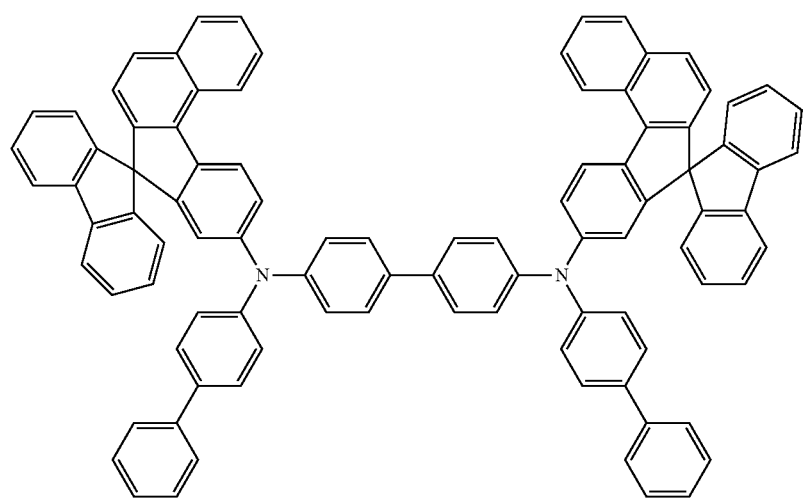
(K3)
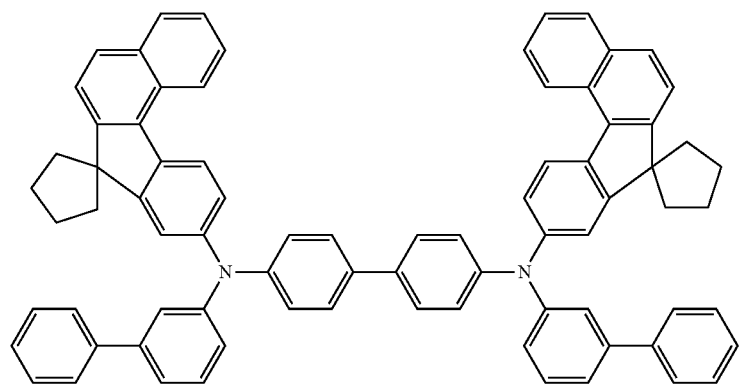
(K4)

-continued
[Chem. 23]
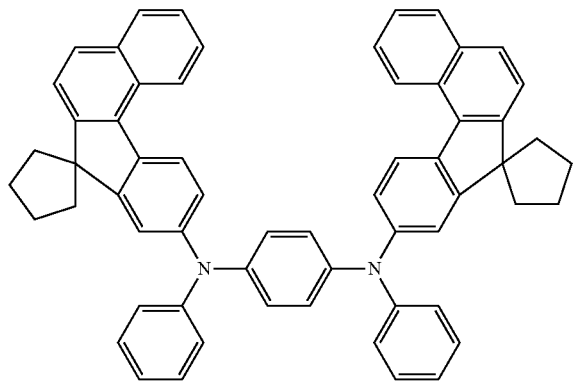
(L1)
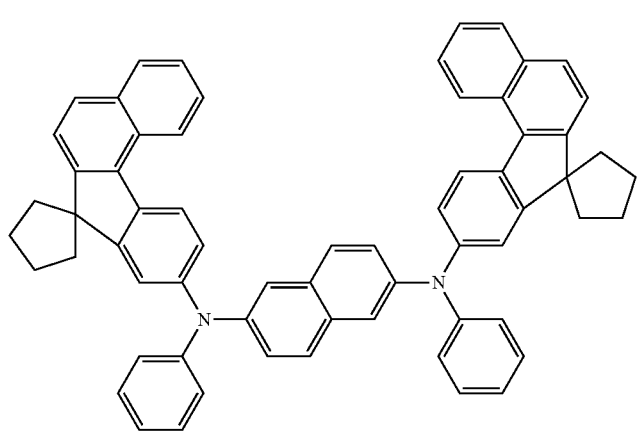
(L2)
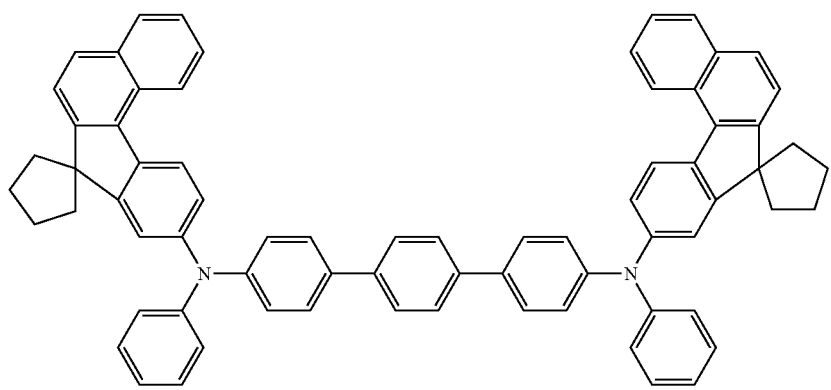
(L3)
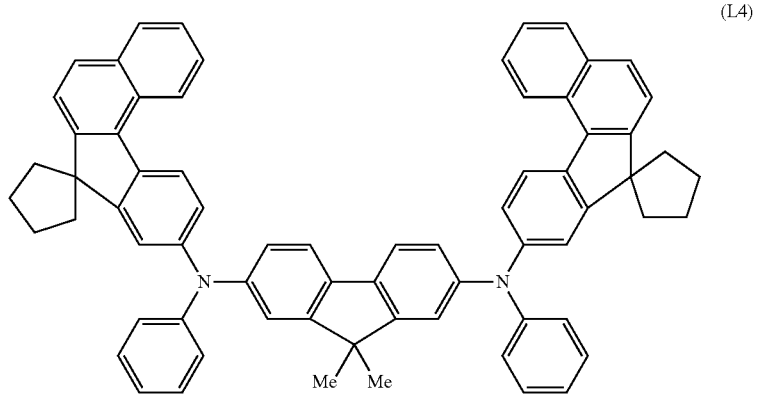
(L4)

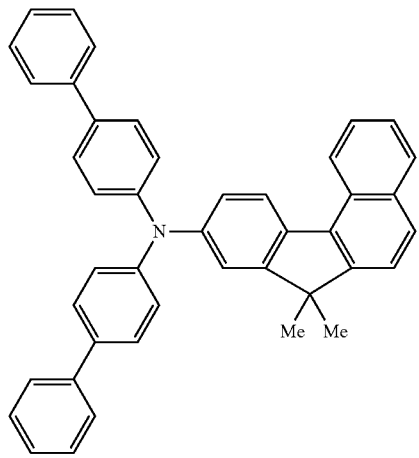
(L5)
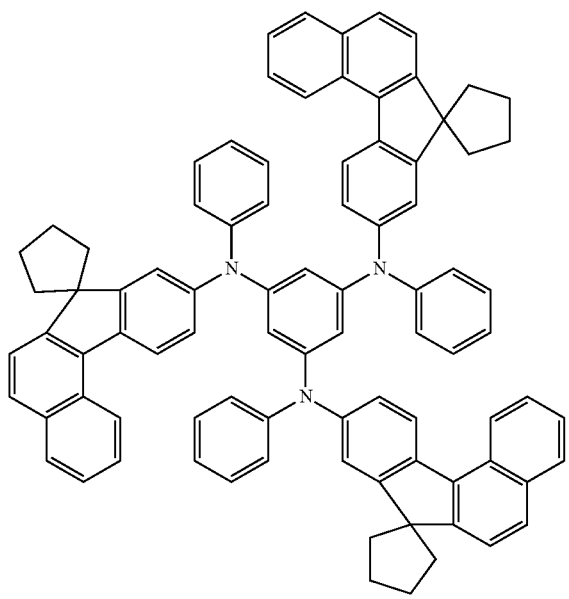
(L6)
[Chem. 24]
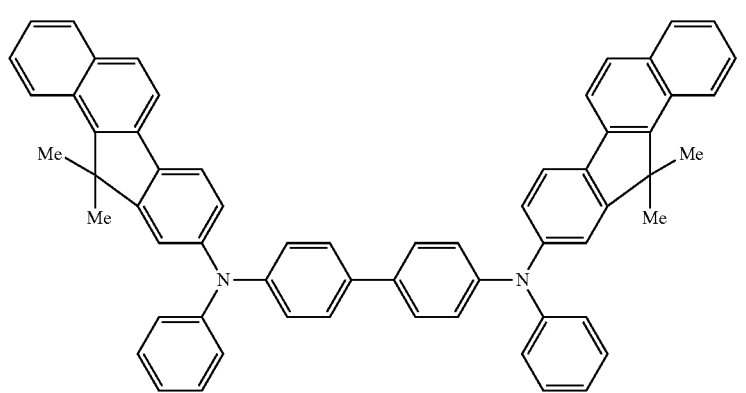
(M1)

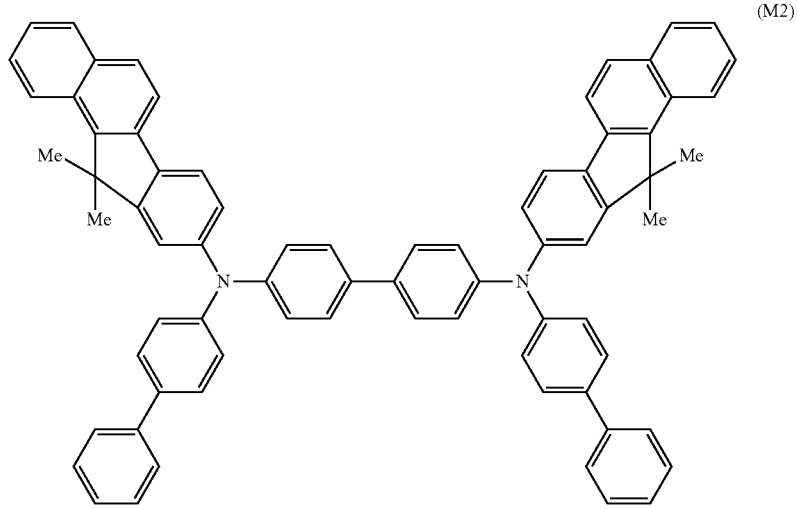
(M2)
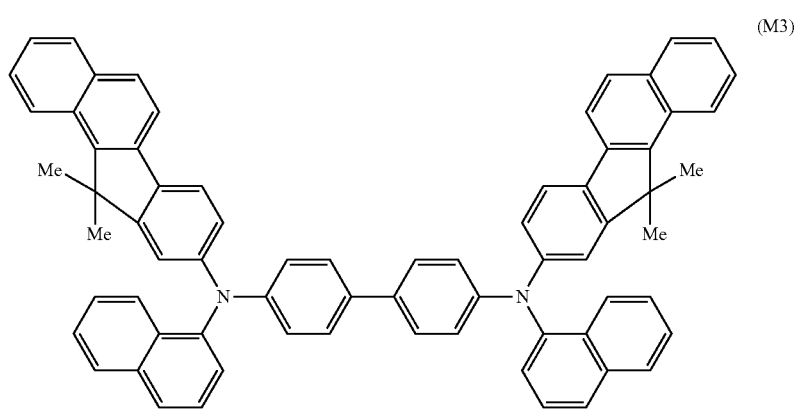
(M3)
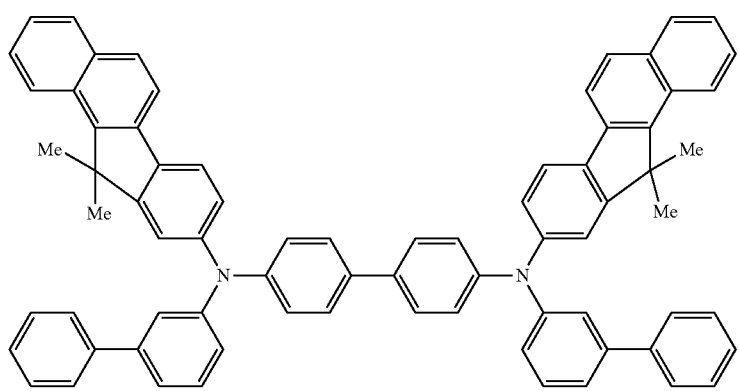
(M4)

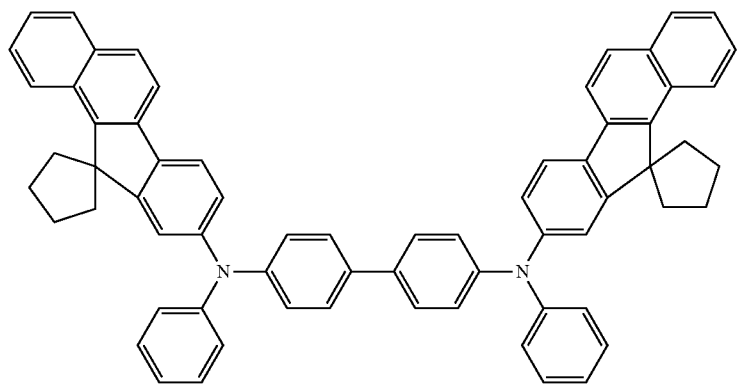
(M5)
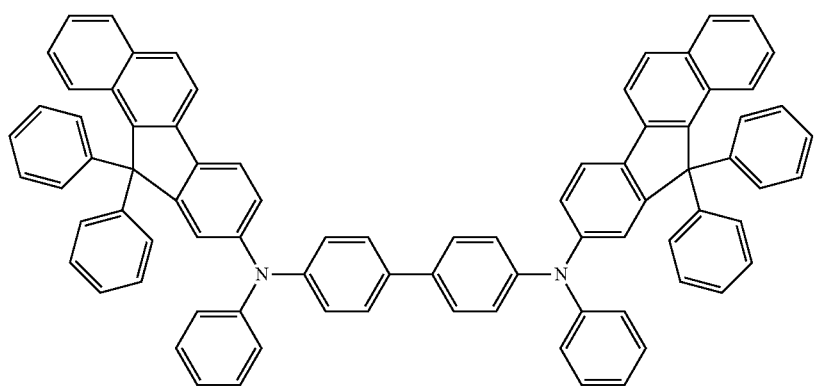
(M6)
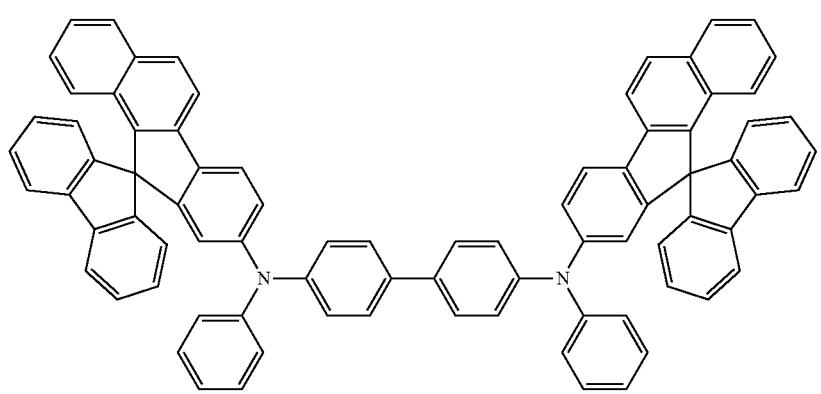
(M7)
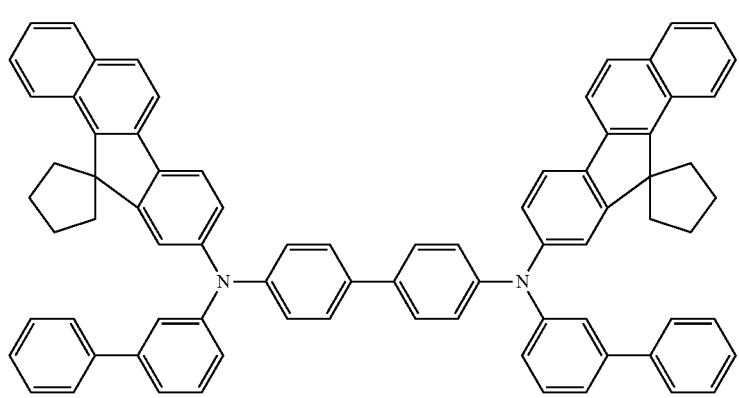
(M8)

[Chem. 25]
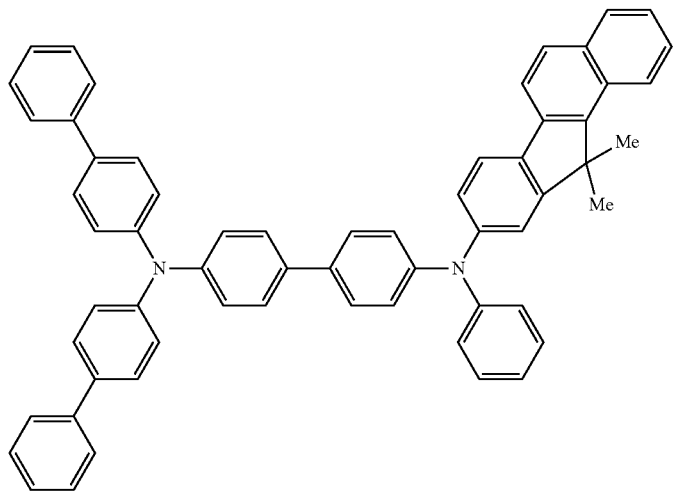
(N1)
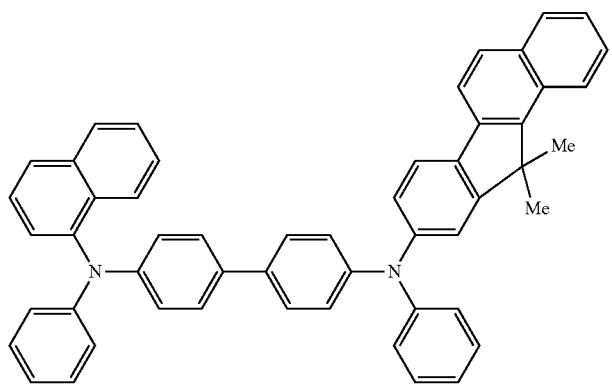
(N2)
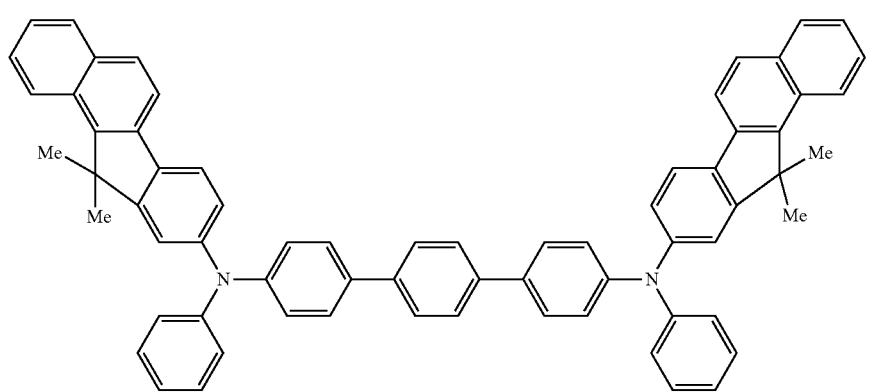
(N3)

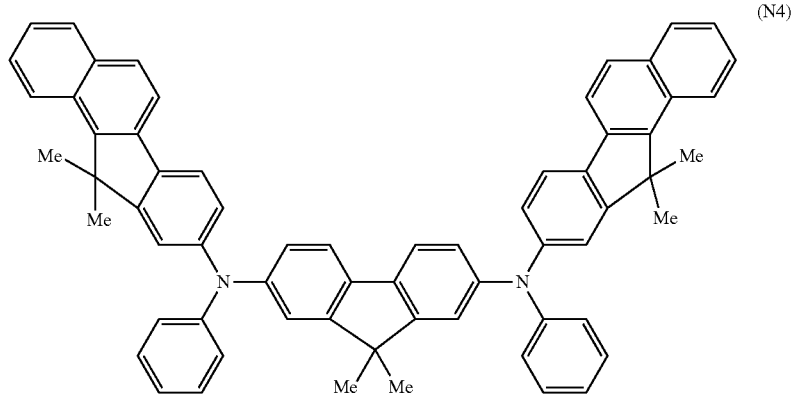
(N4)
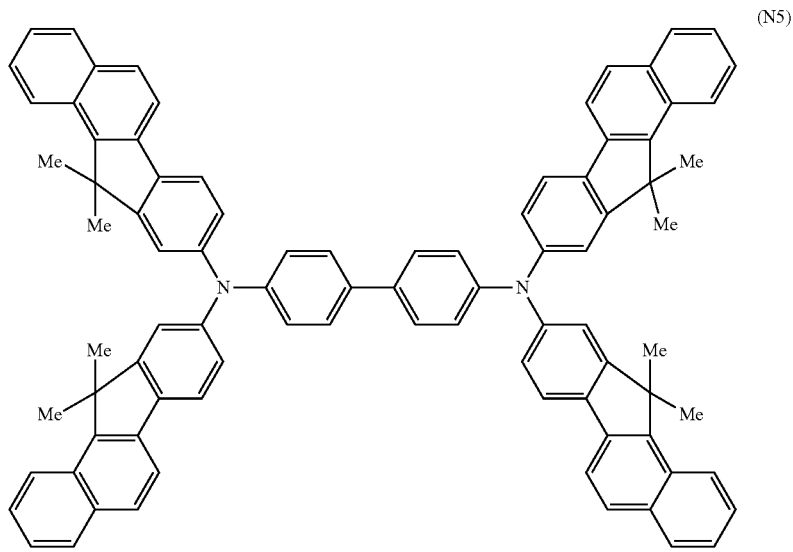
(N5)
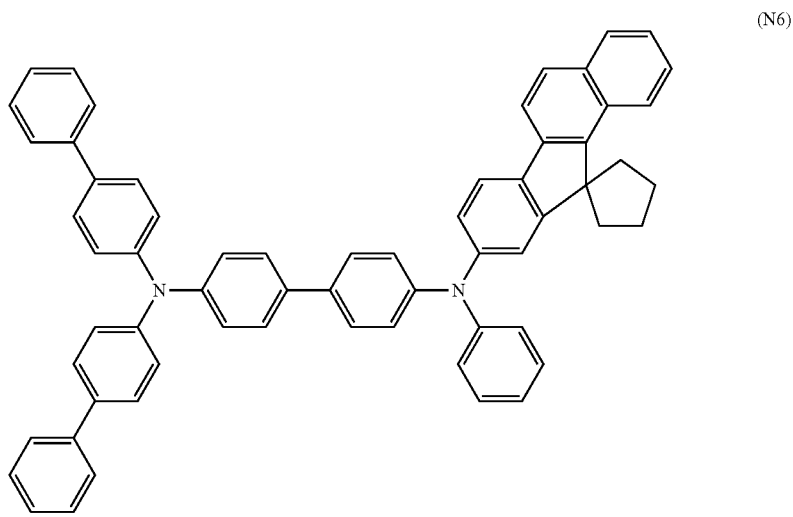
(N6)

(N7)

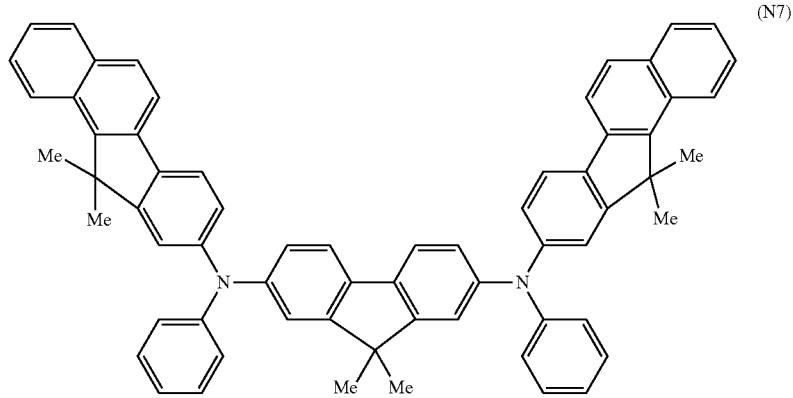

(N8)

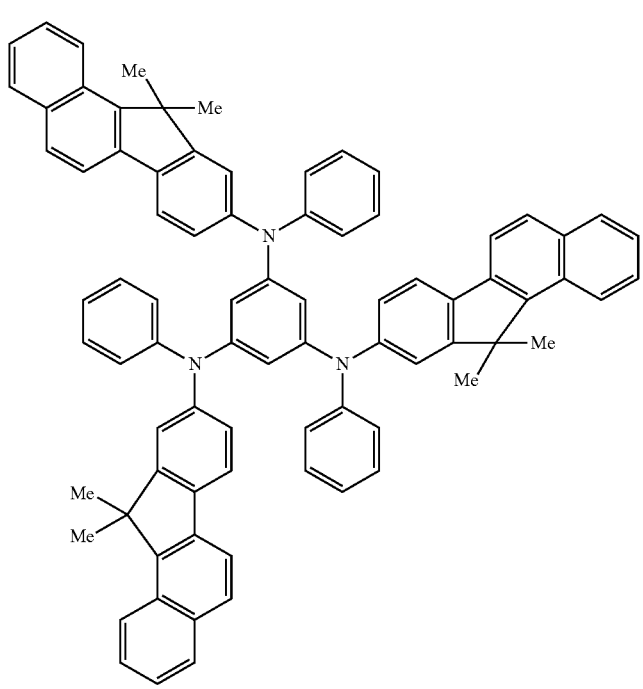

The benzofluorene compound represented by formula (1) can be synthesized by a known method (*Tetrahedron Letters*, 39, 2367 (1998)). For example, it can be synthesized by reacting a dihalobiphenyl compound represented by the following formula (15), in which M is biphenyl, with an amine compound represented by any of the following formulae (16) to (19) in the presence of a base using a copper catalyst or palladium catalyst.

[Chem. 26]

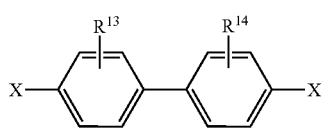
(15)

(In the formula, X represents a halogen atom and $R^{13}$ and $R^{14}$ represent the same substituents as $R^5$ and $R^6$ represented by formula (6).)

[Chem. 27]

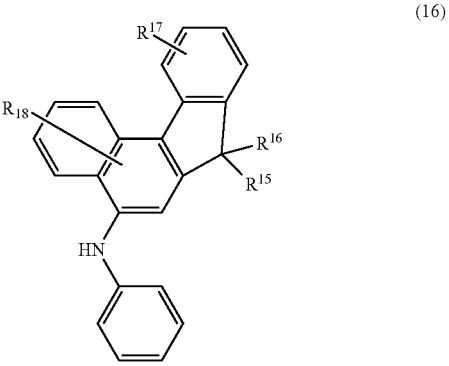
(16)

(17)

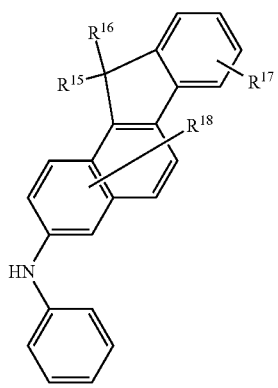

(18)

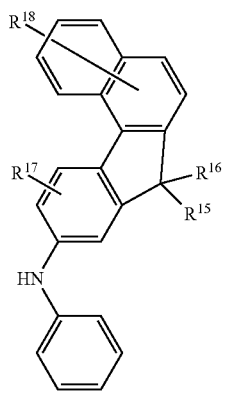

(19)

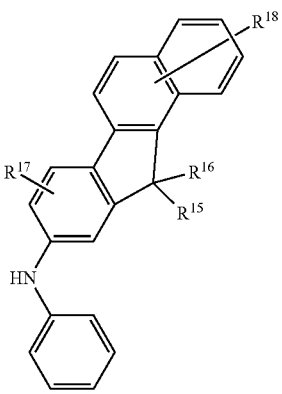

(In the formulae, $R^{15}$ to $R^{18}$ represent the same substituents as $R^1$ to $R^4$ represented by formula (2).)

The benzofluorene compound of the invention is expected to attain a more improved operating voltage and a higher power efficiency than conventional materials. Furthermore, the benzofluorene compound has a high glass transition temperature and is hence expected to further attain an improvement in element life. Consequently, the benzofluorene compound is applicable not only as a hole-injecting material, hole-transporting material, or luminescent material in an organic EL element, electrophotographic photoreceptor, etc., but also in the field of organic photoconductive materials in photo-electric converting elements, solar cells, image sensors, etc.

EXAMPLES

The invention will be explained below in more detail by reference to Examples.

The compounds obtained in the Examples were identified by $^1$H-NMR spectroscopy, $^{13}$C-NMR spectroscopy, and FDMS.

The $^1$H-NMR and $^{13}$C-NMR spectroscopy and the FDMS were conducted respectively with Gemini 200, manufactured by Varian Inc., and M-80B, manufactured by Hitachi, Ltd.

Synthesis Example 1

Synthesis of Compound 1a [See Formula (20) Given Later]

Into a 300-mL eggplant type flask were introduced 46.0 g (455 mmol) of diisopropylamine and 150 mL of dichloromethane. This liquid reaction mixture was cooled to 5° C. or lower. Twenty-five grams (114 mmol) of 2-bromobenzoyl chloride was added dropwise thereto while regulating the reaction temperature so as not to exceed 5° C. Thereafter, the reaction mixture was stirred at room temperature overnight. The resultant liquid reaction mixture was concentrated at ordinary pressure to distill off the dichloromethane or the excess diisopropylamine. Thereafter, toluene and water were added to the residue to conduct extraction. The organic layer was washed with saturated aqueous sodium chloride solution, subsequently dried with anhydrous magnesium sulfate, and then concentrated to isolate 2-bromo-N,N'-diisopropylbenzamide as colorless crystals. This reaction product was used as it was in the succeeding reaction without being purified.

Subsequently, 7.5 g (26.3 mmol) of the 2-bromo-N,N'-diisopropylbenzamide obtained, 5.1 g (29.1 mmol) of 1-naphthylboronic acid, 150 mg (0.13 mmol) of tetrakis(triphenylphosphine)palladium, 38.5 g of 20% by weight aqueous sodium carbonate solution, and 60 mL of tetrahydrofuran were introduced into a 200-mL eggplant type flask. This reaction mixture was heated and stirred overnight with refluxing. The resultant mixture was cooled to room temperature. Thereafter, water was added thereto conduct extraction. The organic layer obtained was washed with saturated aqueous sodium chloride solution, subsequently dried with anhydrous magnesium sulfate, and then concentrated to obtain light-brown crystals. Furthermore, the crystals were purified by silica gel chromatography (solvent: hexane/toluene) to isolate 7.1 g of colorless crystals (yield, 82%). These crystals were ascertained to be the target compound through $^1$H-NMR spectroscopy.

Into a 200-mL eggplant type flask were then introduced 4.0 g (12 mmol) of the 2-(1-naphthyl)-N,N'-diisopropylbenzamide obtained above and 30 mL of tetrahydrofuran. The amide was dissolved. Thereafter, the liquid reaction mixture was cooled to −78° C., and 16 mL of lithium diisopropylamide (1.5-M cyclohexane solution) was added dropwise thereto.

After completion of the dropwise addition, the mixture was stirred for 3 hours while maintaining the temperature and then further stirred at room temperature overnight.

This reaction mixture was treated in an ordinary manner and then treated by silica gel chromatography (solvent: hexane/toluene) to thereby isolate 1.5 g of colorless crystals (yield, 54%) as compound 1a. This reaction product had a melting point of 158-160° C., which agreed with the value in the literature (*J. Org. Chem.*, 56, 5, 1683 (1991)). It was hence identified as benzo[c]fluorenone.

Subsequently, 3.0 g (13 mmol) of the benzo[c]fluorenone, 1.6 g of 98% hydrazine, 2.35 g of sodium hydroxide, and 40 mL of diethylene glycol were introduced into a 200-mL eggplant type flask. The contents were stirred with heating at 160° C. for 18 hours. This liquid reaction mixture was cooled to room temperature and then extracted with chloroform. The extract was dried with magnesium sulfate and then concentrated to obtain dark-brown crystals. Furthermore, the crystals were purified by silica gel chromatography (solvent: hexane/toluene) to isolate 2.4 g of colorless crystals (yield, 85%).

Through $^1$H-NMR spectroscopy and FDMS, the crystals isolated were ascertained to be benzo[c]fluorene.

In 30 mL of chloroform was dissolved 5 g (23.1 mmol) of the benzo[c]fluorene obtained. A small amount of iodine was added thereto. Thereafter, 3.7 g (23.1 mmol) of bromine was added dropwise thereto with stirring at room temperature. After completion of the reaction, the excess bromine was neutralized with sodium thiosulfate and the resultant mixture was extracted with chloroform. The extract was washed with saturated aqueous sodium chloride solution and dried with magnesium sulfate. Thereafter, the extract was concentrated to obtain light-yellow crystals. These crystals were recrystallized with toluene to isolate 5.4 g of compound 2a as colorless crystals (yield, 79%).

[Chem. 28]

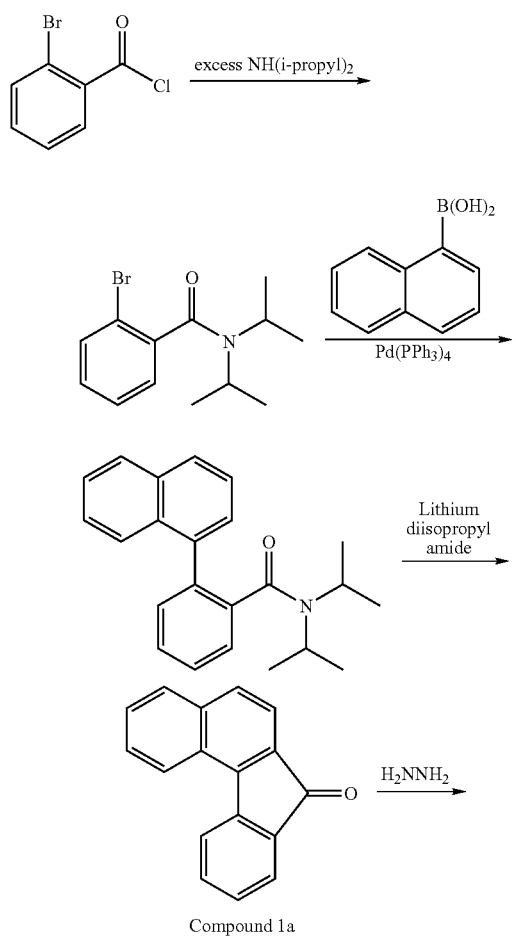

Compound 1a

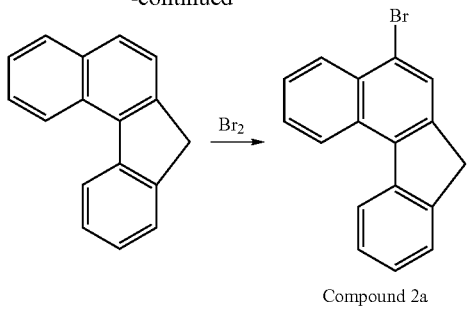

Compound 2a

Synthesis Example 2

Synthesis of Compound 4a [See Formula (21) Given Later]

Into a 200-mL eggplant type flask were introduced 6.45 g (34.9 mmol) of 2-bromobenzaldehyde, 5.0 g (29.1 mmol) of 1-naphthylboronic acid, 0.15 g of tetrakis(triphenylphosphine)palladium, 60 mL of tetrahydrofuran, 10 g (73 mmol) of potassium carbonate, and 20 mL of water. This reaction mixture was heated with refluxing overnight. After washing with saturated aqueous ammonium chloride solution and saturated aqueous sodium chloride solution and drying with anhydrous magnesium sulfate, the extract was concentrated to obtain yellow crystals. These crystals were purified by silica gel chromatography (solvent: hexane/toluene) to obtain 5.4 g of 2-(1-naphthyl)benzaldehyde (yield, 81%).

The reaction product was identified by $^1$H-NMR spectroscopy.

$^1$H-NMR (CDCl$_3$): 9.63 (s, 1H), 8.12 (d, 1H), 7.94 (d, 2H), 7.40-7.71 (m, 8H)

Subsequently, 8.0 g (34.4 mmol) of the 2-(1-naphthyl)benzaldehyde and 50 mL of tetrahydrofuran were introduced into a 200-mL eggplant type flask, and the temperature of the resultant liquid reaction mixture was lowered to −30° C. or below. Thereafter, 38 mL of methylmagnesium chloride (1.4 mol/L solution in toluene/tetrahydrofuran) was added dropwise thereto. Furthermore, the reaction mixture was stirred at −5 to 0° C. for 1 hour and then at room temperature overnight, and 60 mL of 1-N aqueous hydrochloric acid solution was added dropwise thereto to terminate the reaction. Tetrahydrofuran was added to the reaction mixture to extract it. The organic layer obtained was washed with water and saturated aqueous sodium chloride solution and dried with magnesium sulfate. The solvent was distilled off, and the residue was recrystallized with hexane to obtain 7.68 g of Compound 3a (yield, 90% assuming that the purity was 100%; colorless crystals; melting point, 116-118° C.).

$^1$H-NMR spectroscopy revealed that this Compound 3a was a mixture of isomers.

Into a 200-mL eggplant type flask were then introduced 6.0 g (24.2 mmol) of the Compound 3a obtained above and 60 mL of chloroform. Thereafter, 7.4 g (52.3 mmol) of boron trifluoride ether complex was added dropwise thereto at 50° C. The resultant mixture was reacted at that temperature for 5 hours. Eighty milliliters of water was added thereto, and the organic layer was extracted. The organic layer was washed with 100 mL of water three times and further washed with saturated aqueous sodium chloride solution. This organic layer was dried with magnesium sulfate, and the solvent was thereafter distilled off to obtain crude 7-methylbenzo[c]fluorene. Furthermore, this compound was purified by silica gel chromatography (solvent: hexane/toluene) to obtain 3.34 g of 7-methylbenzo[c]fluorene as colorless crystals (yield, 60%; melting point, 81-83° C.).

The reaction product was identified by $^1$H-NMR spectroscopy.

$^1$H-NMR (CDCl$_3$): 8.77 (d, 1H), 8.37 (d, 1H), 7.97 (d, 1H), 7.85 (d, 1H), 7.26-7.70 (m, 6H), 4.02 (1H, q), 1.59 (d, 3H)

Into a 200-mL eggplant type flask were introduced 3.3 g (14.5 mmol) of the 7-methylbenzo[c]fluorene, 70 mL of dimethyl sulfoxide, 5.5 g of 45% aqueous sodium hydroxide solution, and 3.29 g (14.4 mmol) of benzyltriethylammonium chloride. Thereto was dropwise added 4.20 g (29.6 mmol) of methyl iodide at 50° C. Thereafter, the reaction mixture was stirred with heating at that temperature overnight. This reaction mixture was cooled to room temperature, and 100 mL of toluene and 50 mL of water were then added thereto to conduct extraction. The extract was washed with water and saturated aqueous sodium chloride solution and then dried with magnesium sulfate. The organic layer obtained was concentrated to thereby obtain light-brown crystals. Furthermore, the crystals were purified by silica gel chromatography (solvent: hexane/toluene) to thereby obtain Compound 4a as the target compound in a yield of 77%.

The reaction product was identified by $^1$H-NMR spectroscopy and FDMS.

$^1$H-NMR (CDCl$_3$): 8.76 (d, 1H), 8.34 (d, 1H), 7.95 (d, 1H), 7.86 (d, 1H), 7.36-7.67 (m, 6H), 1.55 (s, 6H)

FDMS: 244

[Chem. 29]

(21)

[Chem. 30]

Synthesis Example 3

Synthesis of Compound 5a

Into a 100-mL eggplant type flask were introduced 2.20 g (9.02 mmol) of the Compound 4a obtained in Synthesis Example 2 and 15 mL of dimethylformamide. At room temperature, a dimethylformamide solution of 1.65 g (9.28 mmol) of N-bromosuccinimide (NBS) was added dropwise thereto and the resultant mixture was stirred overnight. Subsequently, 50 mL of toluene and 30 mL of water were added to the liquid reaction mixture to extract the organic layer. The liquid reaction mixture was treated in an ordinary manner and then concentrated to obtain light-brown crystals. The crystals were recrystallized with methanol to obtain 2.55 g of colorless crystals (yield, 88%; melting point, 105-107° C.).

The reaction product was identified by $^1$H-NMR spectroscopy.

$^1$H-NMR (CDCl$_3$): 8.76 (d, 1H), 8.34-8.41 (dd, 2H), 7.93 (s, 1H), 7.38-7.70 (m, 5H), 1.54 (s, 6H)

Synthesis Example 4

Synthesis of Compound 6a

Into a 300-mL eggplant type flask were introduced 10 g (33.9 mmol) of the Compound 2a (5-bromo-7H-benzo[c]fluorene) obtained in Synthesis Example 1, 80 mL of dimethyl sulfoxide, g (6.2 mmol) of benzyltriethylammonium chloride, and 15 g (187 mmol) of 50% sodium hydroxide. A liquid mixture of g (34.2 mmol) of 1,4-dibromobutane and 20 mL of dimethyl sulfoxide was added dropwise thereto. The resultant reaction mixture was stirred at that temperature for 2 hours and further stirred at 80° C. for 5 hours.

To the reaction mixture was added 70 mL of water. Thereafter, 100 mL of toluene was added thereto to conduct extraction. The organic layer was washed with water and saturated aqueous sodium chloride solution and then dried with anhydrous magnesium sulfate. The toluene was distilled off to thereby obtain 10.1 g of a light-yellow viscous oily substance (yield, 85%).

The reaction product was identified by ¹H-NMR spectroscopy and ¹³C-NMR spectroscopy.

¹H-NMR (CDCl₃): 2.17 (br-s, 8H), 7.32-7.67 (m, 5H), 7.91 (s, 1H), 8.29 (d, 1H), 8.37 (d, 1H), 8.74 (d, 1H)

¹³C-NMR (CDCl₃): 27.6, 39.2, 57.5, 122.7, 122.8, 124.1, 125.7, 126.2, 126.9, 127.0, 127.3, 130.3, 131.2, 133.5, 139.6, 153.2, 155.6

[Chem. 31]

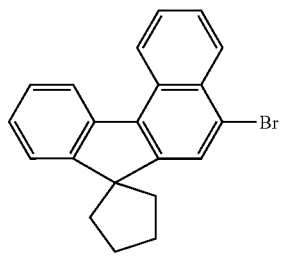

Compound 6a

Synthesis Example 5

Into a 500-mL eggplant type flask were introduced 9.16 g (40.0 mmol) of ethyl 2-bromobenzoate, 8.89 g (44.0 mmol) of 6-methoxynaphthaleneboronic acid, 300 mL of tetrahydrofuran, and 94 g of 20% aqueous sodium carbonate solution. In a nitrogen stream, 0.46 g of tetrakis(triphenylphosphine)palladium was added thereto and the resultant mixture was heated with refluxing overnight. After washing with saturated aqueous ammonium chloride solution and saturated aqueous sodium chloride solution and drying with anhydrous magnesium sulfate, the extract was concentrated to obtain a light-brown oily substance. This oily substance was purified by silica gel chromatography (solvent: hexane/ethyl acetate) to obtain 10.52 g of Compound 1b (colorless oily substance) (yield, 86%).

The reaction product was identified by ¹H-NMR spectroscopy and ¹³C-NMR spectroscopy.

¹H-NMR (CDCl₃): 0.89 (t, 3H, J=7.2 Hz), 3.93 (s, 3H), 4.06 (q, 2H, J=7.2 Hz), 7.11-7.20 (m, 2H), 7.36-7.59 (m, 4H), 7.69-7.78 (m, 3H), 7.85 (d, 1H, J=7.4 Hz)

¹³C-NMR (CDCl₃): 13.8, 55.4, 61.0, 105.6, 119.0, 126.2, 126.7, 127.0, 127.5, 128.7, 129.5, 129.7, 130.9, 131.1, 131.4, 133.6, 136.7, 142.3, 157.7, 168.9

[Chem. 32]

Compound 1b

Subsequently, 9.19 g (30 mmol) of the Compound 1b and 60 mL of cyclopentyl methyl ether were introduced into a 200-mL eggplant type flask. The temperature of the liquid reaction mixture was elevated to 50° C. Thereafter, 56 mL of methylmagnesium chloride (1.4 mol/L solution in toluene/tetrahydrofuran) was added dropwise thereto, and this mixture was stirred at that temperature overnight. The resultant reaction mixture was cooled to room temperature, and 30 mL of water was then added dropwise thereto to terminate the reaction. This reaction mixture was separated into layers. The organic layer was washed with 150 mL of water, and the solvent was distilled off. The residue was purified by silica gel chromatography (solvent: hexane/toluene) to obtain 6.3 g of Compound 2b (colorless solid) (yield, 72%).

Into a 100-mL eggplant type flask were then introduced 3.36 g (11.5 mmol) of the Compound 2b obtained above and 60 mL of chloroform. Thereafter, 2.12 g (15.0 mmol) of boron trifluoride ether complex was added dropwise thereto at 50° C. The resultant mixture was reacted at that temperature for 2 hours and then cooled to room temperature. Thereafter, 30 mL of water was added thereto. This reaction mixture was separated into layers. The organic layer was washed with 150 mL of water, and the solvent was distilled off. The residue was purified by silica gel chromatography (solvent: hexane/toluene) to obtain 2.17 g of Compound 3b as a colorless solid (yield, 68.8%).

The Compounds 2b and 3b were identified by ¹H-NMR spectroscopy and ¹³C-NMR spectroscopy.

<Compound 2b>
¹H-NMR (CDCl₃): 1.47 (s, 6H), 1.90 (br-s, 1H), 3.92 (s, 3H), 7.02-7.48 (m, 6H), 7.60-7.79 (m, 4H)
¹³C-NMR (CDCl₃): 32.7, 55.4, 74.1, 105.7, 119.3, 125.8, 126.0, 126.1, 127.4, 127.7, 128.2, 128.7, 129.4, 132.5, 133.4, 139.0, 139.9, 146.4, 157.8

<Compound 3b>
¹H-NMR (CDCl₃): 1.70 (s, 6H), 3.89 (s, 3H), 7.19-7.28 (m, 2H), 7.28-7.38 (m, 2H), 7.42-7.51 (m, 1H), 7.68-7.78 (d, 2H), 7.84 (d, 1H, J=8.6 Hz), 8.12 (d, 1H, J=9.8 Hz)
¹³C-NMR (CDCl₃): 26.6, 48.6, 55.4, 107.9, 118.7, 119.4, 122.1, 125.3, 125.6, 126.6, 126.9, 127.3, 134.8, 135.3, 139.5, 147.6, 155.0, 156.7

[Chem. 33]

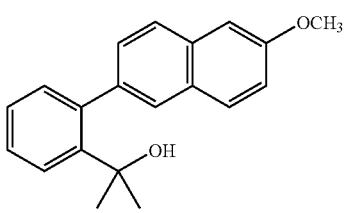

Compound 2b

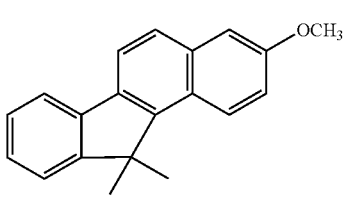

Compound 3b

Subsequently, 2.0 g (7.3 mmol) of the Compound 3b and 20 mL of dichloromethane were introduced into a 100-mL eggplant type flask. The liquid reaction mixture was cooled to 0° C. Boron tribromide was added dropwise thereto while maintaining that temperature. After completion of the dropwise addition, the reaction mixture was stirred at room temperature overnight. Ten milliliters of water was added dropwise thereto with cooling to terminate the reaction. Twenty milliliters of dichloromethane was added to the reaction mixture, which was then separated into layers. Thereafter, the organic layer was washed with 100 mL of water. This organic layer was treated with anhydrous magnesium sulfate and then subjected to silica gel chromatography (solvent: dichloromethane) to obtain 1.84 g of Compound 4b (yield, 97%).

Furthermore, the 4b was reacted with pyridine and trifluoromethanesulfonic anhydride in an ordinary manner to thereby obtain 3.0 g of Compound 5b (yield, 99%).

The reaction products were identified by $^1$H-NMR spectroscopy, $^{13}$C-NMR spectroscopy, and FDMS.

<Compound 4b>

$^1$H-NMR (CDCl$_3$): 1.70 (s, 6H), 5.50 (br-s, 1H), 7.12-7.43 (m, 4H), 7.43-7.60 (m, 1H), 7.60-7.90 (m, 3H) 8.12 (d, 1H, J=8.8 Hz)

$^{13}$C-NMR (CDCl$_3$): 26.6, 48.5, 111.5, 117.7, 119.3, 119.5, 122.1, 125.2, 125.9, 126.5, 128.8, 126.9, 134.7, 135.3, 139.4, 147.6, 152.5, 154.9

<Compound 5b>

$^1$H-NMR (CDCl$_3$): 1.74 (s, 6H), 7.36-7.59 (m, 4H), 7.78-7.96 (m, 3H), 8.02 (d, 1H, J=8.6 Hz), 8.12 (d, 1H, J=9.2 Hz)

FDMS: 392

[Chem. 34]

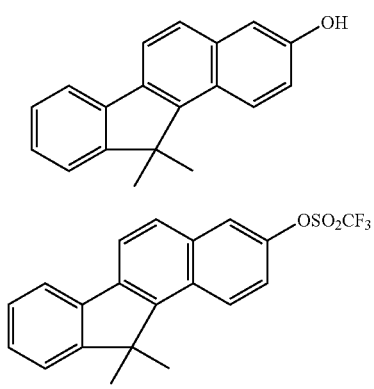

Compound 4b

Compound 5b

Synthesis Example 6

Into a 100-mL eggplant type flask were introduced 1.00 g (3.62 mmol) of 1-(2-(ethoxycarbonyl)phenyl)naphthalene and 10 mL of tetrahydrofuran in a nitrogen atmosphere. The liquid reaction mixture was heated to 5° C. Thereto was dropwise added 7.2 mL of a tetrahydrofuran solution of phenylmagnesium bromide (2 mol/L) over 30 minutes. The resultant mixture was stirred at that temperature for 18 hours and then cooled to room temperature. Subsequently, 20 mL of pure water was added dropwise to the reaction mixture with cooling with ice water. Thereafter, the organic layer was extracted with 30 mL of toluene. Furthermore, the organic layer was washed with pure water and saturated aqueous sodium chloride solution and dried with anhydrous magnesium sulfate. The organic layer obtained was concentrated to thereby isolate 1.46 g of Compound 7a as a yellow oily substance.

Subsequently, 1.45 g of the 7a and 25 mL of acetic acid were introduced into a 100-mL eggplant type flask. Several drops of concentrated sulfuric acid were then added thereto, and the resultant mixture was stirred at room temperature for 18 hours. Thereafter, the liquid reaction mixture was transferred to a separatory funnel. Thirty milliliters of toluene and 20 mL of pure water were added thereto, and the organic layer was extracted. Furthermore, the organic layer was washed with pure water until it became neutral. This organic layer was washed with saturated aqueous sodium chloride solution and then dried with anhydrous magnesium sulfate. The organic layer dried was concentrated, and the resultant residue was purified by silica gel chromatography (solvent: hexane/toluene) to thereby isolate 0.81 g of Compound 8a as a light-yellow powder (yield, 61%).

The reaction product was identified by $^1$H-NMR spectroscopy and FDMS.

$^1$H-NMR (CDCl$_3$): 7.21-7.33 (m, 11H), 7.46-7.89 (m, 7H), 8.36-8.40 (d, 1H), 8.77-8.81 (d, 1H)

FDMS: 368

Subsequently, the Compound 8a was brominated according to Synthesis Example 3 to thereby isolate Compound 9a.

This compound was identified by FDMS.

FDMS: 446

[Chem. 35]

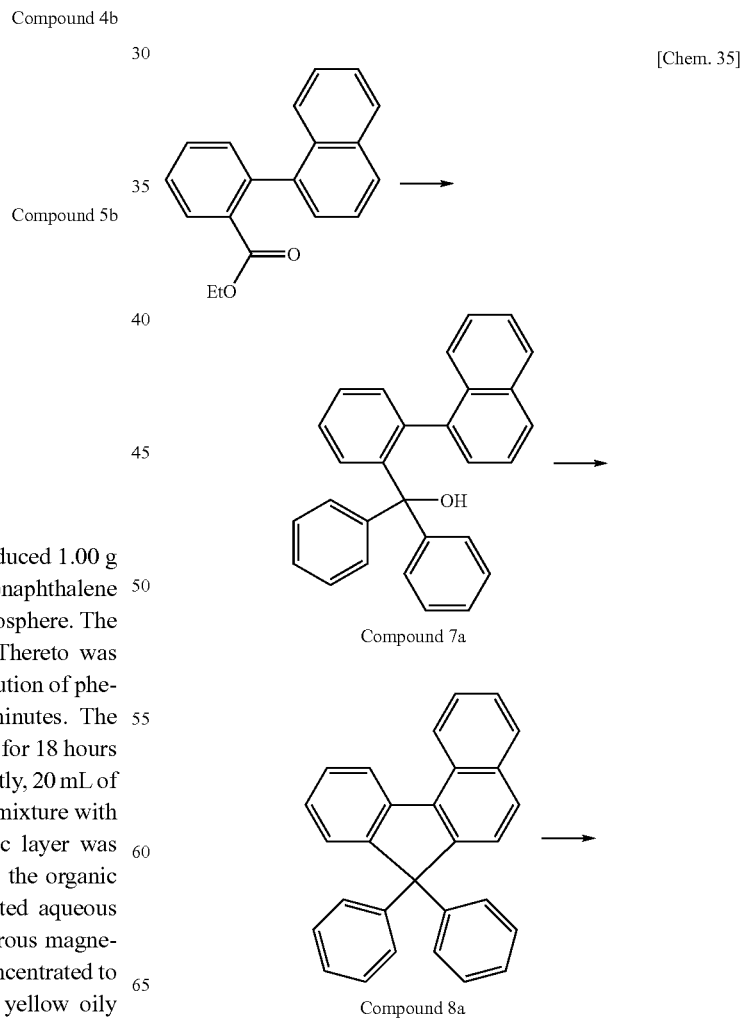

Compound 7a

Compound 8a

-continued

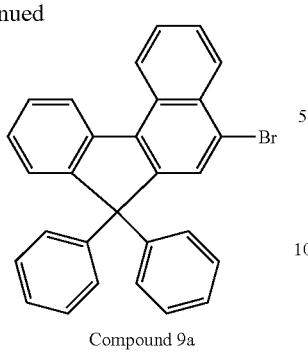

Compound 9a

Synthesis Example 7

Into a 300-mL eggplant type flask were introduced 12 g (33.8 mmol) of 2-bromo-6-(2-ethoxycarbonyl)phenyl)naphthalene (6b) and 120 mL of dehydrated tetrahydrofuran. Thereto was dropwise added 60 mL of a tetrahydrofuran solution of phenylmagnesium bromide (2 mol/L) at room temperature. After completion of the dropwise addition, the resultant mixture was stirred with heating at 50° C. overnight. This liquid reaction mixture was cooled to room temperature, and 100 g of 10% aqueous ammonium chloride solution was added thereto to terminate the reaction. The organic layer was washed with 50 g of pure water three times and then dried with magnesium sulfate. This organic layer was filtered and concentrated to thereby obtain 17.3 g of Compound 7b as an orange-colored oily substance. The 7b was used as it was in the succeeding step.

Into a 100-mL eggplant type flask were introduced 3.46 g (6.76 mmol) of the 7b obtained above and 14 mL of acetic acid. The contents were stirred at room temperature overnight. Thereafter, the liquid reaction mixture was transferred to a separatory funnel. Fifty milliliters of toluene and 50 mL of pure water were added thereto, and the organic layer was extracted. Furthermore, the organic layer was washed with pure water until it became neutral. This organic layer was washed with saturated aqueous sodium chloride solution and then dried with anhydrous magnesium sulfate. The organic layer dried was concentrated, and the resultant residue was purified by silica gel chromatography (solvent: hexane/toluene) to thereby isolate 1.3 g of Compound 8b as a white powder (yield, 42%).

The reaction product was identified by $^1$H-NMR spectroscopy and FDMS.

$^1$H-NMR (CDCl$_3$): 8.02 (d, 2H), 7.81-7.88 (m, 2H), 7.60 (d, 1H), 7.18-7.46 (m, 14H)

FDMS: 446

[Chem. 36]

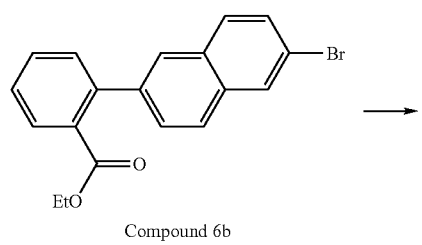

Compound 6b

-continued

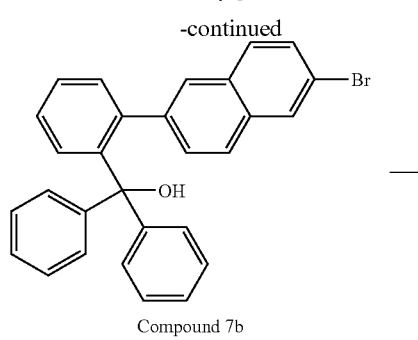

Compound 7b

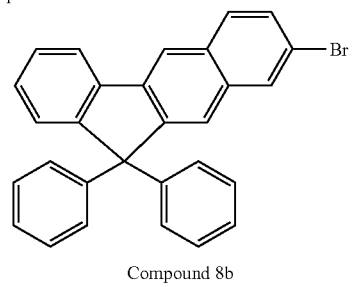

Compound 8b

Example 1

Synthesis of Compound (A1)

In 40 mL of xylene were suspended 2 g (6.2 mmol) of the Compound 5a obtained in Synthesis Example 3, 0.58 g (6.2 mmol) of aniline, and 0.83 g of sodium tert-butoxide using a 100-mL eggplant type flask. The atmosphere in the system was replaced by nitrogen. Furthermore, in a nitrogen atmosphere, mg of palladium acetate and 8 mg of tri-tert-butylphosphine were added thereto and the resultant mixture was heated to 125° C. This liquid reaction mixture was aged at a given temperature for 20 hours and then cooled to room temperature. Twenty milliliters of water was added thereto, and extraction was then conducted. The organic phase was concentrated. The concentrate obtained was used as it was in the succeeding step without being purified.

Subsequently, 3.0 g (7.4 mmol) of 4,4'-diiodobiphenyl, 5.1 g (15.2 mmol) of the 5-phenylamino-7,7-dimethyl-7H-benzo[c]fluorene obtained above, and 1.7 g (17.7 mmol) of sodium tert-butoxide were suspended in 50 mL of xylene using a 200-mL eggplant type flask. The atmosphere in the system was replaced by nitrogen. Furthermore, in a nitrogen atmosphere, 3 mg of palladium acetate and 8 mg of tri-tert-butylphosphine were added thereto and the resultant mixture was heated to 125° C. This liquid reaction mixture was aged at a given temperature for 20 hours and then cooled to room temperature. Twenty milliliters of water was added thereto, and extraction was then conducted. The organic layer was concentrated. The residue was recrystallized with toluene to obtain 4.98 g of Compound (A1) (yield, 82%).

The compound (A1) had a glass transition temperature of 162° C., which was higher by at least about 40° C. than the glass transition temperatures of 4,4'-bis[N-(1-naphthyl)-N-phenylamino]biphenyl, 2,7-bis[N-(1-naphthyl)-N-phenylamino]-9,9'-dimethylfluorene, and N,N'-di[2-(9,9-dimethylfluorenyl)]-N,N'-di(4-biphenyl)benzidine (i.e., 96° C., 110° C., and 120° C., respectively), which are conventional materials.

Example 2

Synthesis of Compound (B3)

The same procedure as in Example 1 was conducted, except that the Compound 6a synthesized in Synthesis Example 4 was used in place of the Compound 5a. Thus, 5.0 g of compound (B3) was isolated (yield, 78%).

Example 3

Synthesis of Compound (F1)

Into a 300-mL eggplant type flask were introduced 894 mg (9.6 mmol) of aniline, 923 mg (9.6 mmol) of sodium tert-butoxide, 44 mg (0.048 mmol) of tris(dibenzylideneacetone)dipalladium, 160 mg (0.288 mmol) of bis(diphenylphosphino)ferrocene, and 130 mL of toluene in a nitrogen atmosphere. This liquid reaction mixture was heated to 80° C. Thereafter, a toluene (30 mL) solution of 2.51 g (6.4 mmol) of the Compound 5b synthesized in Synthesis Example 5 was added dropwise thereto over 30 minutes, and the resultant mixture was stirred at that temperature overnight. This reaction mixture was cooled to room temperature. Thereafter, 200 mL of water was added thereto to terminate the reaction. This reaction mixture was separated into layers. The organic layer was washed with 600 mL of water and treated with anhydrous magnesium sulfate, and the solvent was then distilled off. The residue was purified by silica gel chromatography (solvent: hexane/toluene) to obtain 1.76 g of the target secondary amine as a slightly purple solid (yield, 81%).

This compound was identified by $^1$H-NMR spectroscopy and FDMS.

$^1$H-NMR (CDCl$_3$): 1.74 (s, 6H), 5.88 (br-s, 1H), 6.94-7.04 (m, 1H), 7.12-7.40 (m, 7H), 7.42-7.58 (m, 2H), 7.62-7.86 (m, 3H), 8.12 (d, 1H, J=9.2 Hz)

FDMS: 335

Subsequently, 1.76 g (5.25 mmol) of the secondary amine, 1.02 g (2.5 mmol) of 4,4'-diiodobiphenyl, 505 mg (5.25 mmol) of sodium tert-butoxide, 11.8 mg (0.053 mmol) of palladium acetate, and 60 mL of o-xylene were introduced into a 100-mL eggplant type flask in a nitrogen atmosphere. To this liquid reaction mixture was dropwise added 0.21 mL of a toluene solution of tri(tert-butyl)phosphine (0.21 mmol). Thereafter, the liquid reaction mixture was heated to 120° C. After 2 hours, the mixture was cooled to room temperature, and 200 mL of water was added thereto to terminate the reaction. This reaction mixture was separated into layers. The organic layer was washed with 600 mL of water and treated with anhydrous magnesium sulfate, and the solvent was then distilled off. The residue was purified by silica gel chromatography (solvent: hexane/toluene) to obtain 1.89 g of Compound (F1) as a slightly yellow solid (yield, 92%; melting point, 292° C.).

This compound was identified by $^1$H-NMR spectroscopy and FDMS.

$^1$H-NMR (CDCl$_3$): 1.72 (s, 12H), 7.00-7.12 (br-t, 2H), 7.12-7.68 (m, 28H), 7.70-7.86 (m, 4H), 8.10 (d, 2H, J=9.2 Hz)

FDMS: 820

Incidentally, the Compound (F1) had a glass transition temperature of 172° C., which was higher by at least about 50° C. than the glass transition temperatures of 4,4'-bis[N-(1-naphthyl)-N-phenylamino]biphenyl, 2,7-bis[N-(1-naphthyl)-N-phenylamino]-9,9'-dimethylfluorene, and N,N'-di[2-(9,9-dimethylfluorenyl)]-N,N'-di(4-biphenyl)benzidine (i.e., 96° C., 110° C., and 120° C., respectively), which are conventional materials.

Example 4

Synthesis of Compound (B2)

In 25 mL of xylene were suspended 3.31 g (7.43 mmol) of the Compound 9a obtained in Synthesis Example 6, 1.22 g (3.63 mmol) of N,N'-diphenylbenzidine, and 0.84 g of sodium tert-butoxide. The atmosphere in the system was replaced by nitrogen. Furthermore, in a nitrogen atmosphere, 8 mg of palladium acetate and 32 mg of tri-tert-butylphosphine were added thereto and the resultant mixture was heated to 125° C. This liquid reaction mixture was aged at a given temperature for 20 hours and then cooled to room temperature. Twenty milliliters of water was added thereto, and extraction was then conducted. The organic layer was concentrated. The residue was recrystallized with toluene to obtain 2.36 g of Compound (B2) as a yellow powder (yield, 61%).

This compound was identified by FDMS.

FDMS: 1,068

Example 5

Synthesis of Compound (F6)

The same reaction as in Example 4 was conducted, except that the Compound 8b obtained in Synthesis Example 7 was used in place of the Compound 9a. Thus, Compound (F6) was synthesized.

This compound was identified by FDMS.

FDMS: 1,068

Example 6

Production of Element

A glass substrate having an ITO transparent electrode having a thickness of 130 nm was subjected to ultrasonic cleaning successively in acetone and isopropyl alcohol. Subsequently, the glass substrate was cleaned with boiling isopropyl alcohol and then dried. Furthermore, the substrate was treated with UV/ozone. The substrate thus treated was used as a transparent conductive supporting substrate. Copper phthalocyanine was deposited in a film thickness of 25 nm on the ITO transparent electrode by vacuum deposition. Subsequently, Compound (A1) was deposited in a film thickness of 45 nm by vacuum deposition to form a hole-transporting layer. Aluminum trisquinolinol complex was then deposited in a film thickness of 60 nm by vacuum deposition to form an electron-transporting layer. For depositing those organic compounds, the same deposition conditions were used which included a degree of vacuum of $1.0 \times 10^{-4}$ Pa and a deposition rate of 0.3 nm/sec.

Subsequently, LiF and aluminum were deposited as a cathode in thicknesses of 0.5 nm and 100 nm, respectively. Thus, a metallic electrode was formed.

Furthermore, in a nitrogen atmosphere, a glass substrate for protection was superposed on the coated substrate, and the resultant assemblage was sealed with a UV-curing resin. A direct-current voltage of 4.5 V was applied to the element thus obtained, with the ITO electrode and the LiF—Al electrode as the positive electrode and the negative electrode, respectively.

As a result, a current density of 7.5 mA/cm² was obtained and a green luminescence having a luminance of 401 cd/m² was observed.

Comparative Examples 1 and 2

Elements were produced in the same manner as in Example 6, except that NPD or 2,7-bis(naphthylphenylamino)-9,9-dimethylfluorene was used in place of the Compound (A1).

The results of evaluation concerning efficiency and life in operation at a current density of 7.5 mA/cm² are shown in Table 1.

age of 5.67V, current efficiency of 4.5 cd/A, and power efficiency of 2.5 lm/W. The results of the evaluation are shown in Table 2.

Example 8

The same element as in Example 7 was produced, except that the Compound (F1) was replaced by Compound (A1). This element was operated under the conditions of a constant current density of 20 mA/cm². Values in this operation are shown in Table 2.

TABLE 1

| | | Operating voltage V | Current efficiency cd/A | Power efficiency lm/W | Element life[1] hr |
|---|---|---|---|---|---|
| Example 6 | compound (A1) | 4.5 | 5.2 | 3.7 | 756 |
| Comparative Example 1 | NPD | 5.3 | 4.1 | 2.4 | 408 |
| Comparative Example 2 | (2,7-bis(naphthylphenylamino)-9,9-dimethylfluorene) | 5.1 | 3.6 | 1.6 | 102 |

[1]Lapse of time to a 10% decrease in luminance

Example 7

The same procedure as in Example 6 was conducted, except that Compound (F1) was used in place of the Compound (A1) for forming a hole-transporting layer. Thus, an organic EL element was produced. This element was examined under the conditions of a constant current density of 20 mA/cm². As a result, the element showed an operating volt- Comparative Example 3

The same element as in Example 7 was produced, except that the Compound (F1) was replaced by NPD. This element was operated under the conditions of a constant current density of 20 mA/cm². Values in this operation are shown in Table 2.

TABLE 2

| | Compound | Tg °C. | Luminance cd/m² | Color of luminescence | Operating voltage V | Current efficiency cd/A | Power efficiency lm/W | Luminance half-life period hr |
|---|---|---|---|---|---|---|---|---|
| Example 7 | (F1) | 172 | 925 | green | 5.67 | 4.5 | 2.5 | 2850 |
| Example 8 | (A1) | 162 | 1035 | green | 5.24 | 5.18 | 3.12 | 1900 |
| Comparative Example 3 | NPD | 96 | 928 | green | 6.09 | 4.5 | 2.4 | 1420 |

Example 9

A glass substrate having an ITO transparent electrode having a thickness of 130 nm was subjected to ultrasonic cleaning successively in acetone and isopropyl alcohol. Subsequently, the glass substrate was cleaned with boiling isopropyl alcohol and then dried. Furthermore, the substrate was treated with UV/ozone. The substrate thus treated was used as a transparent conductive supporting substrate. Copper phthalocyanine was deposited in a film thickness of 25 nm on the ITO transparent electrode by vacuum deposition. Subsequently, Compound (A1) was deposited in a film thickness of 45 nm by vacuum deposition to form a hole-transporting layer. Subsequently, TBADN and TBPe were co-deposited by vapor deposition as a host and a dopant, respectively, in a weight ratio of 99:1 to form a film having a thickness of 40 nm. Aluminum trisquinolinol complex was then deposited in a film thickness of 20 nm by vacuum deposition to form an electron-transporting layer. For depositing those organic compounds, the same deposition conditions were used which included a degree of vacuum of $1.0 \times 10^{-4}$ Pa and a deposition rate of 0.3 nm/sec.

Subsequently, LiF and aluminum were deposited as a cathode in thicknesses of 0.5 nm and 100 nm, respectively. Thus, a metallic electrode was formed.

Furthermore, in a nitrogen atmosphere, a glass substrate for protection was superposed on the coated substrate, and the resultant assemblage was sealed with a UV-curing resin. The element thus obtained was operated under the constant-current-density conditions of 20 mA/cm$^2$, with the ITO electrode and the LiF—Al electrode as the positive electrode and the negative electrode, respectively. In this operation, the luminance, operating voltage, current efficiency, power efficiency, and luminance half-life period were 940 cd/m$^2$, 5.51 V, 4.7 cd/A, 2.7 lm/W, and 450 hr, respectively. The results are shown in Table 3.

[Chem. 37]

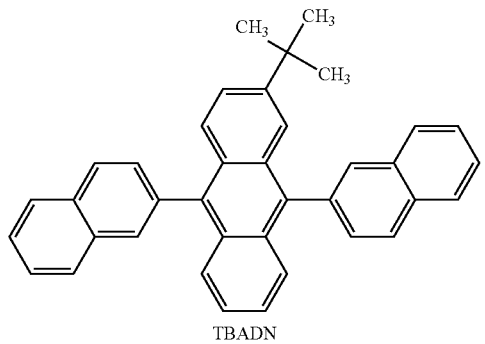

TBADN

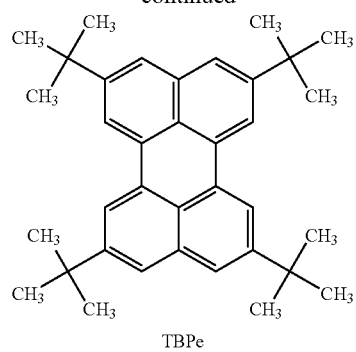

TBPe

Example 10

The same element as in Example 9 was produced, except that the Compound (A1) was replaced by Compound (F1). This element was operated under the conditions of a constant current density of 20 mA/cm$^2$. Values in this operation are shown in Table 3.

Example 11

The same element as in Example 9 was produced, except that the Compound (A1) was replaced by Compound (F6). This element was operated under the conditions of a constant current density of 20 mA/cm$^2$. Values in this operation are shown in Table 3.

Comparative Example 4

The same element as in Example 9 was produced, except that the Compound (A1) was replaced by NPD. This element was operated under the conditions of a constant current density of 20 mA/cm$^2$. Values in this operation are shown in Table 3.

TABLE 3

| | Compound | Luminance cd/m$^2$ | Color of luminescence | Operating voltage V | Current efficiency cd/A | Power efficiency lm/W | Luminance half-life period hr |
|---|---|---|---|---|---|---|---|
| Example 9 | (A1) | 940 | blue | 5.51 | 4.7 | 2.7 | 450 |
| Example 10 | (F1) | 740 | blue | 6.22 | 3.5 | 1.9 | 650 |
| Example 11 | (F6) | 758 | blue | 6.17 | 3.7 | 2.2 | 740 |
| Comparative Example 4 | NPD | 773 | blue | 6.54 | 3.9 | 1.9 | 460 |

Synthesis Example 8

Synthesis of Compound 2c [See Formula (22) Given Later]

Into a 300-mL eggplant type flask were introduced 18.6 g (100 mmol) of 2'-hydroxy-1'-acetonaphthone, 100 mL of dichloromethane, and 39.6 g (500 mmol) of pyridine. This liquid reaction mixture was cooled to 5° C. or lower. Thereto was dropwise added 31.0 g (110 mmol) of trifluoromethanesulfonic anhydride while regulating the reaction temperature so as not to exceed 5° C. Thereafter, the reaction mixture was stirred at room temperature overnight. Water was added to this liquid reaction mixture, and the resultant mixture was separated into layers. The organic layer was washed with 3.5% aqueous hydrochloric acid solution and water, subsequently dried with anhydrous magnesium sulfate, and concentrated to isolate 32.7 g of 1'-acetonaphthone 2'-trifluoromethanesulfonate as a slightly yellow oily substance. This reaction product was used as it was in the succeeding reaction without being purified.

Subsequently, 15.1 g (47.5 mmol) of the 1'-acetonaphthone 2'-trifluoromethanesulfonate obtained, 7.8 g (50.0 mmol) of 4-chlorophenylboronic acid (purity, 95%), 549 mg (0.475 mmol) of tetrakis(triphenylphosphine)palladium, 100.7 g of 20% by weight aqueous sodium carbonate solution, and 250 mL of tetrahydrofuran were introduced into a 500-mL eggplant type flask. This reaction mixture was stirred with heating at 60° C. overnight. The resultant mixture was cooled to room temperature and then separated into layers. The organic layer obtained was washed with water, dried with anhydrous magnesium sulfate, and then concentrated to obtain 12.4 g of light-yellow crystals. Through $^1$H-NMR spectroscopy, these crystals were ascertained to be 2'-(4-chlorophenyl)-1'-acetonaphthone, i.e., the target compound. This reaction product was used as it was in the succeeding reaction without being purified.

$^1$H-NMR (200 MHz, CDCl$_3$): 2.12 (3H, s), 7.33-7.65 (7H, m), 7.78-8.01 (3H, m)

$^{13}$C-NMR (50 MHz, CDCl$_3$): 32.9, 124.7, 126.5, 127.1, 127.6, 128.3, 128.8, 128.9, 129.5, 130.6, 132.6, 134.3, 134.4, 138.4, 138.7, 207.1

Into a 300-mL eggplant type flask were then introduced 9.8 g (35 mmol) of the 2'-(4-chlorophenyl)-1'-acetonaphthone obtained above, 70 mL of tetrahydrofuran, and 70 mL of ethanol. The crystals were dissolved. Thereafter, 6.6 g (175 mmol) of sodium boron hydride was added thereto. The resultant mixture was stirred at room temperature for 8 hours.

A hundred grams of 10% aqueous ammonium chloride solution was added to the reaction mixture while taking care of foaming. Thereafter, the mixture was concentrated under vacuum. The residue was extracted with 200 mL of toluene. The resultant extract was washed with water, dried with anhydrous magnesium sulfate, and then concentrated to obtain 9.4 g of light-yellow crystals. Through $^1$H-NMR spectroscopy, these crystals were ascertained to be 1-(1-hydroxy)ethyl-2-(4-chlorophenyl)naphthalene, i.e., the target compound. This reaction product was used as it was in the succeeding reaction without being purified.

$^1$H-NMR (200 MHz, CDCl$_3$): 1.71 (3H, d, J=7.0 Hz), 2.05 (1H, br-s), 5.35 (1H, q, J=7.0 Hz), 7.16-7.63 (7H, m), 7.69-7.95 (2H, m), 8.76-8.93 (1H, br-d)

$^{13}$C-NMR (50 MHz, CDCl$_3$): 23.9, 68.9, 125.8, 125.9, 127.0, 127.8, 127.9, 128.4, 128.8, 130.4, 130.8, 133.2, 134.2, 136.9, 137.1, 140.6

Subsequently, 2.8 g (10 mmol) of the 1-(1-hydroxy)ethyl-2-(4-chlorophenyl)naphthalene obtained above and 20 mL of chloroform were introduced into a 100-mL eggplant type flask. The contents were cooled to 0° C. Thereafter, 1.85 g (13 mmol) of boron trifluoride diethyl etherate was added dropwise thereto, and the resultant mixture was stirred at room temperature for 1 hour.

Twenty grams of water was added to the reaction mixture to terminate the reaction. Thereafter, the organic layer was washed with water, dried with anhydrous magnesium sulfate, and then concentrated to obtain 2.7 g of a light-yellow solid. Through $^1$H-NMR spectroscopy, this solid was ascertained to be 9-chloro-11-methyl-11H-benzo[a]fluorene (compound 1c), i.e., the target compound. This reaction product was used as it was in the succeeding reaction without being purified.

$^1$H-NMR (200 MHz, CDCl$_3$): 1.66 (3H, d, J=7.2 Hz), 4.33 (1H, q, J=7.2 Hz), 7.32-7.65 (5H, m), 7.70 (1H, d, J=8.1 Hz), 7.80-8.01 (3H, m), 8.06 (1H, d, J=8.0 Hz)

In 20 mL of dimethyl sulfoxide were dissolved 2.7 g (10 mmol) of the 9-chloro-11-methyl-11H-benzo[a]fluorene obtained, 2.3 g (10 mmol) of benzyltriethylammonium chloride, and 4.3 g (30 mmol) of methyl iodide. This solution was cooled to 0° C. Thereafter, 1.2 g (30 mmol) of 48% aqueous sodium hydroxide solution was added dropwise thereto with stirring. The resultant mixture was stirred at room temperature for 1 hour, and 50 mL of toluene was then added thereto. Subsequently, the organic layer was washed with water. This organic layer was dried with magnesium sulfate, and the extract was then concentrated to obtain light-yellow crystals. These crystals were subjected to silica gel column chromatography (eluent: hexane) to isolate 2.0 g of 9-chloro-11,11-dimethyl-11H-benzo[a]fluorene (Compound 2c) as white crystals (yield, 72%).

$^1$H-NMR (200 MHz, CDCl$_3$): 1.73 (6H, s), 7.21-7.66 (5H, m), 7.69 (1H, d, J=7.8 Hz), 7.80-7.99 (3H, m), 8.19 (1H, d, J=8.3 Hz)

$^{13}$C-NMR (50 MHz, CDCl$_3$): 26.3, 48.8, 118.6, 120.6, 122.8, 124.0, 125.0, 126.2, 127.2, 128.7, 130.0, 132.7, 134.0, 135.6, 137.8, 147.1, 157.0

[Chem. 38]

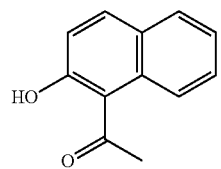

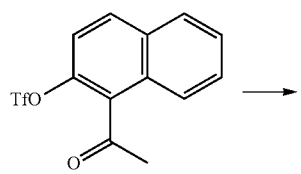

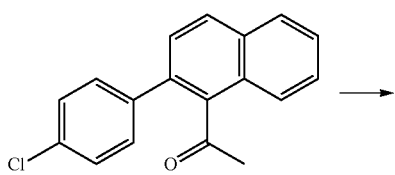

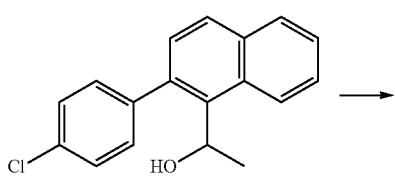

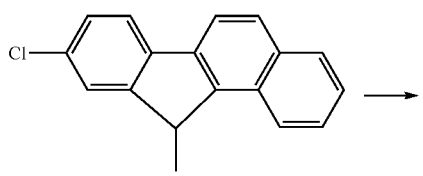

Compound 1c

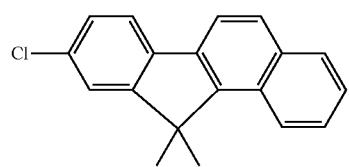

Compound 2c

Example 12

Synthesis of Compound M1

In 40 mL of xylene were suspended 736 mg (2.64 mmol) of 9-chloro-11,11-dimethyl-11H-benzo[a]fluorene, 404 mg (1.2 mmol) of N,N'-diphenylbenzidine, and 461 mg of sodium tert-butoxide in a 100-mL eggplant type flask. The atmosphere in the system was replaced by nitrogen. Furthermore, in a nitrogen atmosphere, 2.25 mg of palladium acetate and 7 mg of tri-tert-butylphosphine were added to the suspension and the resultant mixture was heated to 125° C. This liquid reaction mixture was aged at a given temperature for 15 hours and then cooled to room temperature. Twenty milliliters of water was added thereto, and the resultant mixture was extracted with dichloromethane. The organic phase was washed with water and then concentrated. The residue was purified by silica gel column chromatography to obtain 974 mg of Compound (M1) as a light-ocher powder (yield, 99%).

This compound was identified by FDMS and $^1$H-NMR spectroscopy.

FDMS: m/z=820

$^1$H-NMR (200 MHz, CDCl$_3$): 1.68 (12H, s), 6.98-7.75 (36H, m), 7.85 (4H, s), 7.95 (2H, d, J=8.0 Hz), 8.18 (2H, d, J=8.0 Hz)

The Compound (M1) had a glass transition temperature of 154° C., which was higher by at least about 30° C. than the glass transition temperatures of 4,4'-bis[N-(1-naphthyl)-N-phenylamino]biphenyl, 2,7-bis[N-(1-naphthyl)-N-phenylamino]-9,9'-dimethylfluorene, and N,N'-di[2-(9,9-dimethylfluorenyl)]-N,N'-di(4-biphenyl)benzi dine (i.e., 96° C., 110° C., and 120° C., respectively), which are conventional materials.

Example 13

Production of Element

A glass substrate coated with an ITO transparent electrode (anode) having a thickness of 110 nm was subjected to ultrasonic cleaning in a neutral detergent, pure water, and acetone. Thereafter, the glass substrate was cleaned with boiling isopropyl alcohol. Furthermore, the substrate was cleaned with ultraviolet and ozone. The glass substrate cleaned was set in a vacuum deposition apparatus, which was then evacuated with a vacuum pump to 1×10$^{-4}$ Pa. Copper phthalocyanine was vapor-deposited on the ITO transparent electrode at a deposition rate of 0.3 nm/sec to form a 20-nm hole-injecting layer. Subsequently, compound (M1) was vapor-deposited at a deposition rate of 0.3 nm/sec in a thickness of 30 nm to form a hole-transporting layer. Tris(8-quinolinolato) aluminum was successively vapor-deposited at a deposition rate of 0.3 nm/sec in a thickness of 50 nm to form a luminescent layer. Subsequently, silver and magnesium were co-deposited by vapor deposition (weight ratio, 10:1) at a deposition rate of 0.33 nm/sec in a thickness of 100 nm, and silver was further vapor-deposited at a deposition rate of 0.2 nm/sec in a thickness of 10 nm to form a cathode. Thus, an organic EL element was produced.

The luminance, operating voltage, current efficiency, and power efficiency of the element operated at current densities of 10 mA/cm$^2$ and 20 mA/cm$^2$ are shown in Table 4.

Comparative Example 5

The same element as in Example 13 was produced, except that the Compound (M1) was replaced by NPD.

The luminance, operating voltage, current efficiency, and power efficiency of the element operated at current densities of 10 mA/cm$^2$ and 20 mA/cm$^2$ are shown in Table 4.

TABLE 4

| | Compound | Current density mA/cm$^2$ | Luminance cd/m$^2$ | Voltage V | Current efficiency cd/A | Power lm/W |
|---|---|---|---|---|---|---|
| Example 13 | M1 | 10 | 319 | 6.0 | 2.97 | 1.56 |
| | | 20 | 646 | 6.5 | 3.05 | 1.48 |
| Comparative Example 5 | NPD | 10 | 296 | 6.3 | 2.91 | 1.46 |
| | | 20 | 600 | 6.8 | 3.02 | 1.40 |

While the invention has been described in detail and with reference to specific embodiments thereof, it will be apparent to one skilled in the art that various changes and modifications can be made therein without departing from the spirit and scope thereof.

This application is based on a Japanese patent application filed on Apr. 13, 2006 (Application No. 2006-110765) and a Japanese patent application filed on Jul. 24, 2006 (Application No. 2006-201097), the contents thereof being herein incorporated by reference.

INDUSTRIAL APPLICABILITY

According to the invention, a novel material having a lower operating voltage and longer-lasting durability than conventional materials can be provided. More specifically, a novel benzofluorene compound suitable for use as a hole-injecting material, hole-transporting material, and luminescent material in organic EL elements, etc. can be provided.

The invention claimed is:

1. A benzofluorene compound represented by formula (1):

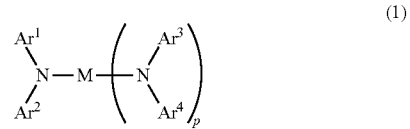

wherein M is biphenyl framework; $Ar^1$ to $Ar^4$ each independently is an unsubstituted phenyl group, an unsubstituted phenylphenyl group, an unsubstituted naphthyl group, an unsubstituted fluorenyl group, an unsubstituted anthryl group, or a substituent represented by any of the following formulae (2) to (5) which does not have any substituent other than $R^1$ to $R^4$, provided that at least one of $Ar^1$ to $Ar^4$ is a substituent represented by any of formulae (2) to (5); and p is 1

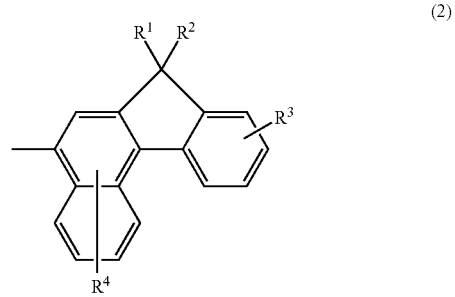

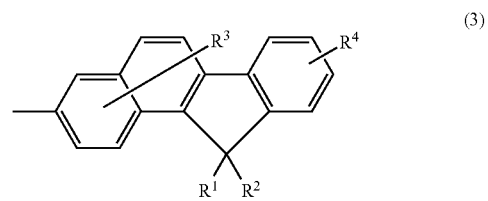

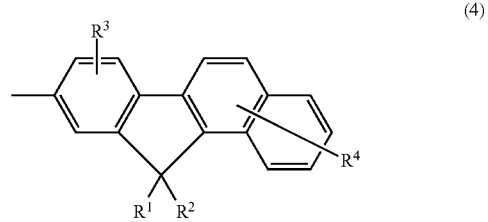

-continued (5)

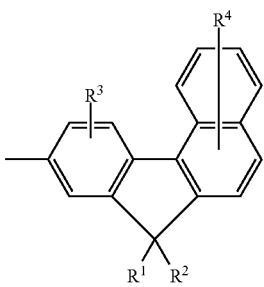

wherein $R^1$ and $R^2$ each independently is a hydrogen atom, a linear, branched, or cyclic alkyl group having 1-18 carbon atoms, or a phenyl group, and $R^3$ and $R^4$ each independently is a hydrogen atom or a phenyl group, provided that $R^1$ and $R^2$ may be bonded to each other to form a ring.

2. A benzofluorene compound as claimed in claim 1, represented by the following formula (6):

(6)

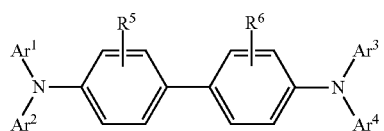

wherein $R^5$ and $R^6$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms; and $Ar^1$ to $Ar^4$ are the same as defined in formula (1).

3. A benzofluorene compound according to claim 2, wherein at least one of $Ar^1$ to $Ar^4$ is a substituent represented by formula (4).

4. An organic electroluminescent element comprising the benzofluorene compound according to claim 2 in any of a luminescent layer, a hole-transporting layer, and a hole-injecting layer.

5. An organic electroluminescent element comprising the benzofluorene compound according to claim 1 in any of a luminescent layer, a hole-transporting layer, and a hole-injecting layer.

6. The benzofluorene compound according to claim 1, wherein at least one of $Ar^1$ to $Ar^4$ is a substituent represented by formula (2).

7. The benzofluorene compound according to claim 1, wherein at least one of $Ar^1$ to $Ar^4$ is a substituent represented by formula (3).

8. The benzofluorene compound according to claim 1, wherein at least one of $Ar^1$ to $Ar^4$ is a substituent represented by formula (4).

9. The benzofluorene compound according to claim 1, wherein at least one of $Ar^1$ to $Ar^4$ is a substituent represented by formula (5).

10. A benzofluorene compound according to claim 1, represented by formula (A1)

(A1)

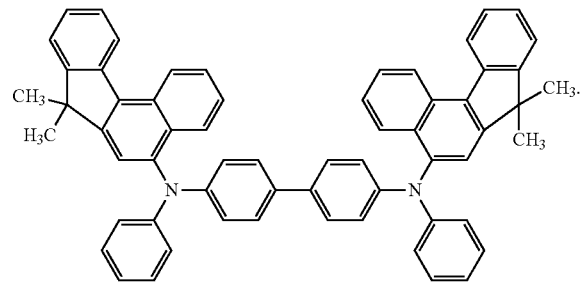

11. A benzofluorene compound according to claim 1, represented by formula (B2)

(B2)

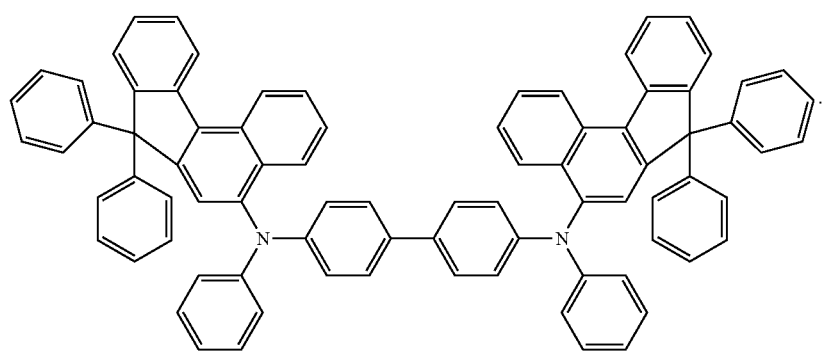

12. A benzofluorene compound according to claim 1, represented by formula (B3)
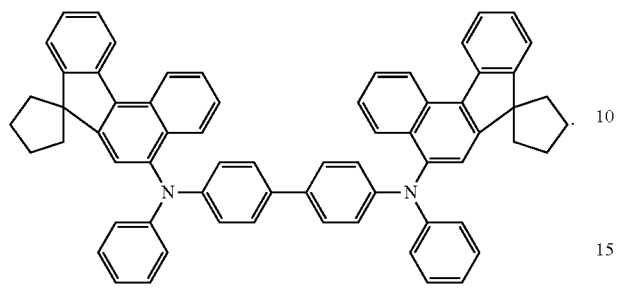
13. A benzofluorene compound according to claim 1, represented by formula (F1)
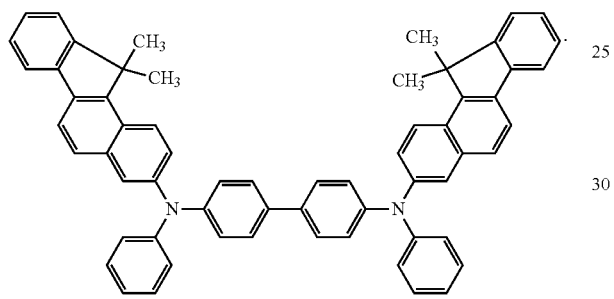
14. A benzofluorene compound according to claim 1, represented by formula (F6)
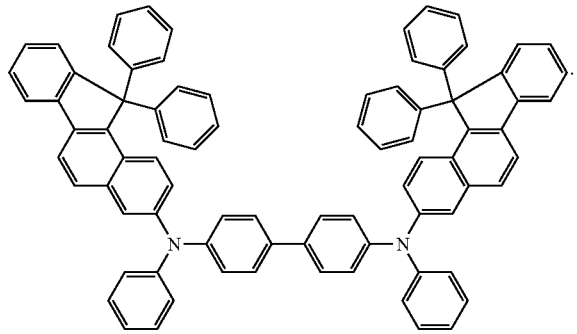
15. A benzofluorene compound represented by any of formulae (7) to (10):
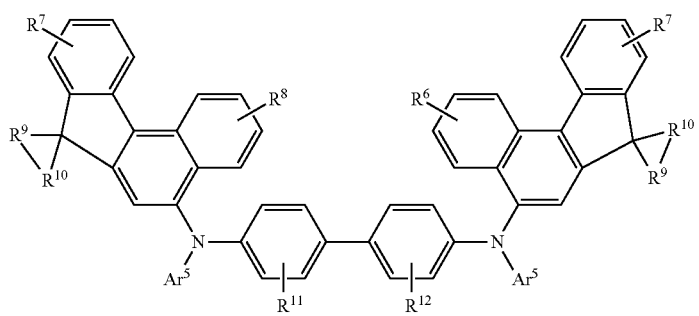
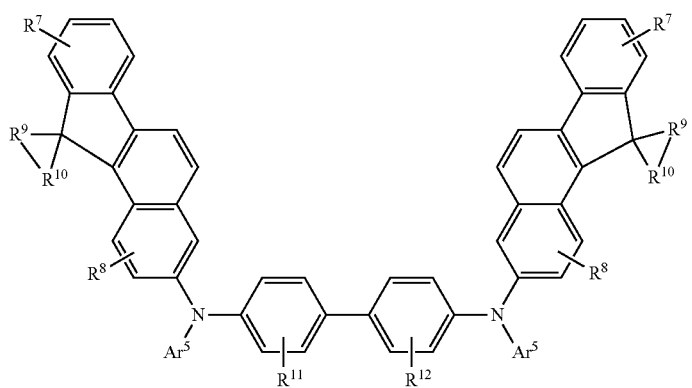

-continued (9)

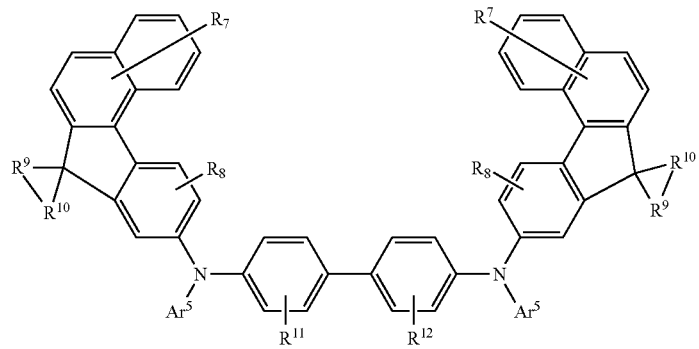

(10)

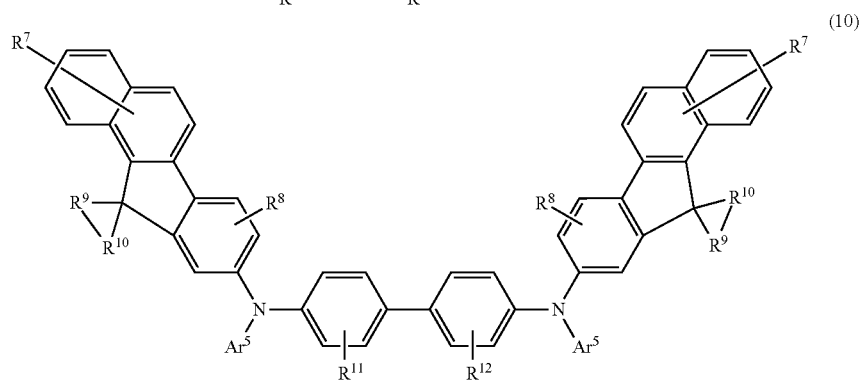

wherein $R^7$, $R^8$, $R^{11}$, and $R^{12}$ each independently is a hydrogen atom, a halogen atom, a substituted or unsubstituted amino group, a linear, branched, or cyclic alkyl group, a linear, branched, or cyclic alkoxy group, a substituted or unsubstituted aryl group having 6-40 carbon atoms, or a substituted or unsubstituted aryloxy group having 6-40 carbon atoms; $R^9$ and $R^{10}$ represent an alkylene group having 1-6 carbon atoms or an arylene group having 6-12 carbon atoms; and $Ar^5$ represents a substituted or unsubstituted aryl group having 6-40 carbon atoms or a substituted or unsubstituted heteroaryl group having 5-40 carbon atoms.

16. An organic electroluminescent element comprising the benzofluorene compound according to claim 15 in any of a luminescent layer, a hole-transporting layer, and a hole-injecting layer.

17. A benzofluorene compound according to claim 15, represented by formula (10).

18. A compound represented by formula (M1):

(M1)

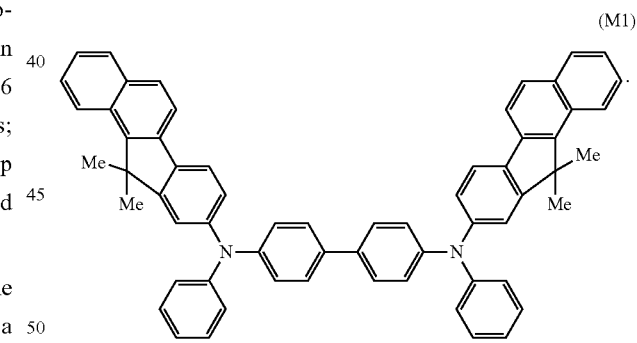

* * * * *